US012714766B2

(12) United States Patent
Jaros et al.

(10) Patent No.: US 12,714,766 B2
(45) Date of Patent: Aug. 25, 2026

(54) METHOD OF IN VITRO CHONDROCYTE AND CARTILAGE CULTURE TO OBTAIN MATERIAL FOR THE TREATMENT OF ARTICULAR CARTILAGE DEFECTS

(71) Applicant: ARTHEC S.A., Gdansk (PL)

(72) Inventors: Sławomir Jaros, Łódź (PL); Grzegorz Sobieraj, Łódź (PL); Julita Balcerek, Konstantynów Łódzki (PL)

(73) Assignee: ARTHEC S.A., Gdańsk (PL)

( * ) Notice: Subject to any disclaimer, the term of this patent is extended or adjusted under 35 U.S.C. 154(b) by 886 days.

(21) Appl. No.: 17/632,141

(22) PCT Filed: Aug. 3, 2020

(86) PCT No.: PCT/EP2020/071826
§ 371 (c)(1),
(2) Date: Feb. 1, 2022

(87) PCT Pub. No.: WO2021/023718
PCT Pub. Date: Feb. 11, 2021

(65) Prior Publication Data

US 2022/0265899 A1 Aug. 25, 2022

(30) Foreign Application Priority Data

Aug. 2, 2019 (PL) ........................................ 430801

(51) Int. Cl.

| | |
|---|---|
| ***A61L 27/38*** | (2006.01) |
| ***A61K 35/00*** | (2006.01) |
| ***A61K 35/32*** | (2015.01) |
| ***A61L 27/36*** | (2006.01) |
| ***A61P 19/04*** | (2006.01) |
| ***C12N 5/071*** | (2010.01) |
| ***C12N 5/077*** | (2010.01) |
| ***C12N 9/50*** | (2006.01) |

(52) U.S. Cl.
CPC .......... *A61L 27/3817* (2013.01); *A61K 35/00* (2013.01); *A61K 35/32* (2013.01); *A61L 27/3612* (2013.01); *A61P 19/04* (2018.01); *C12N 5/0655* (2013.01); *C12N 5/0697* (2013.01); *C12N 9/50* (2013.01); *A61L 2430/06* (2013.01); *C12N 2501/105* (2013.01); *C12N 2501/15* (2013.01); *C12N 2533/90* (2013.01)

(58) Field of Classification Search
CPC .................................................. A61L 27/3817
See application file for complete search history.

(56) References Cited

U.S. PATENT DOCUMENTS

2003/0099620 A1 5/2003 Zaleske et al.
2006/0210643 A1 9/2006 Truncale et al.

FOREIGN PATENT DOCUMENTS

RU 2 677 688 C1 1/2019

OTHER PUBLICATIONS

Stokes, David G., et al. "Regulation of type-Il collagen gene expression during human chondrocyte de-differentiation and recovery of chondrocyte-specific phenotype in culture involves Sry-type high-mobility-group box (SOX) transcription factors." Biochemical Journal 360.2 (2001): 461-470. (Year: 2001).*
Peretti, Giuseppe M., et al. "Bonding of cartilage matrices with cultured chondrocytes: an experimental model." Journal of orthopaedic research 16.1 (1998): 89-95. (Year: 1998).*
Millipore Sigma Website, https://www.sigmaaldrich.com/US/en/technical-documents/technical-article/cell-culture-and-cell-culture-analysis/mammalian-cell-culture/f-12-ham?srsltid=AfmBOooFKZUxBVvr_gpNaz5VQ6wYZ8vp3xDXgX9rMe44Z9ytLiE4GdRh (accessed: Oct. 18, 2024) (Year: 2024).*
Lee, Seung Yun, et al. "Review of the current research on fetal bovine serum and the development of cultured meat." Food science of animal resources 42.5 (2022): 775. (Year: 2022).*
Vacanti, Charles A., et al. "Joint resurfacing with cartilage grown in situ from cell-polymer structures." The American journal of sports medicine 22.4 (1994): 485-488. (Year: 1994).*
Obradovic, B., et al. "Integration of engineered cartilage." Journal of Orthopaedic Research 19.6 (2001): 1089-1097. (Year: 2001).*
Stokes, David G., et al. "Regulation of type-II collagen gene expression during human chondrocyte de-differentiation and recovery of chondrocyte-specific phenotype in culture involves Sry-type high-mobility-group box (SOX) transcription factors." Biochemical Journal 360.2 (2001): 461-470. (Year: 2001).*
Rönn et al., Arthritis 2011.1 (2011): 454873 (Year: 2011).*
Sacitharan et al., Experimental & Molecular Medicine 50.9 (2018): 1-10. (Year: 2018).*
Lane et al., Arthritis research & therapy 17.1 (2015): 54. (Year: 2015).*
Merriam-Webster's definition of viable, https://www.merriam-webster.com/dictionary/viable, accessed: Nov. 4, 2025 (Year: 2025).*
Fox et al. Sports health 1.6 (2009): 461-468. (Year: 2009).*
PCT International Patent Application Publication No. WO 2006/050213 A2, (Michalow, A. E. [US/US]) , published Mar. 11, 2006.
Cavalli, E. et al., "Characterization of polydactyly chondrocytes and their use in cartilage engineering", Scientific Reports, 2019, vol. 9, pp. 1-15.
Guillén-García, P. et al., "Viability of Pathologic Cartilage Fragments as a Source for Autologous Chondrocyte Cultures", Cartilage, 2016, vol. 7, pp. 149-156.
Hayes, A. J. et al., "Macromolecular Organization and In Vitro Growth Characteristics of Scaffold-free Neocartilage Grafts", Journal of Histochemistry & Cytochemistry, 2007, vol. 55, No. 8, pp. 853-866.

(Continued)

*Primary Examiner* — Maria G Leavitt
*Assistant Examiner* — Brendan Thomas Tinsley
(74) *Attorney, Agent, or Firm* — Gary J. Gershik

(57) ABSTRACT

The present invention relates to a new method for treating human or animal tissue such as cartilage, particularly damaged tissue. More specifically, the invention relates to a method to obtain material for treating the damaged tissue, for example any cartilage damage, in particular as a result of traumatic or degenerative cartilage damage.

18 Claims, 5 Drawing Sheets

(56) References Cited

OTHER PUBLICATIONS

Figure 1:
Figure 1:
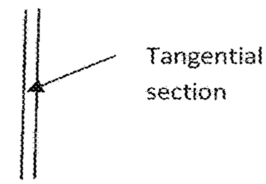
Figure 1:
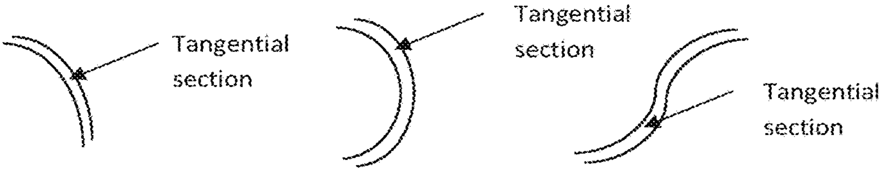
Figure 1:
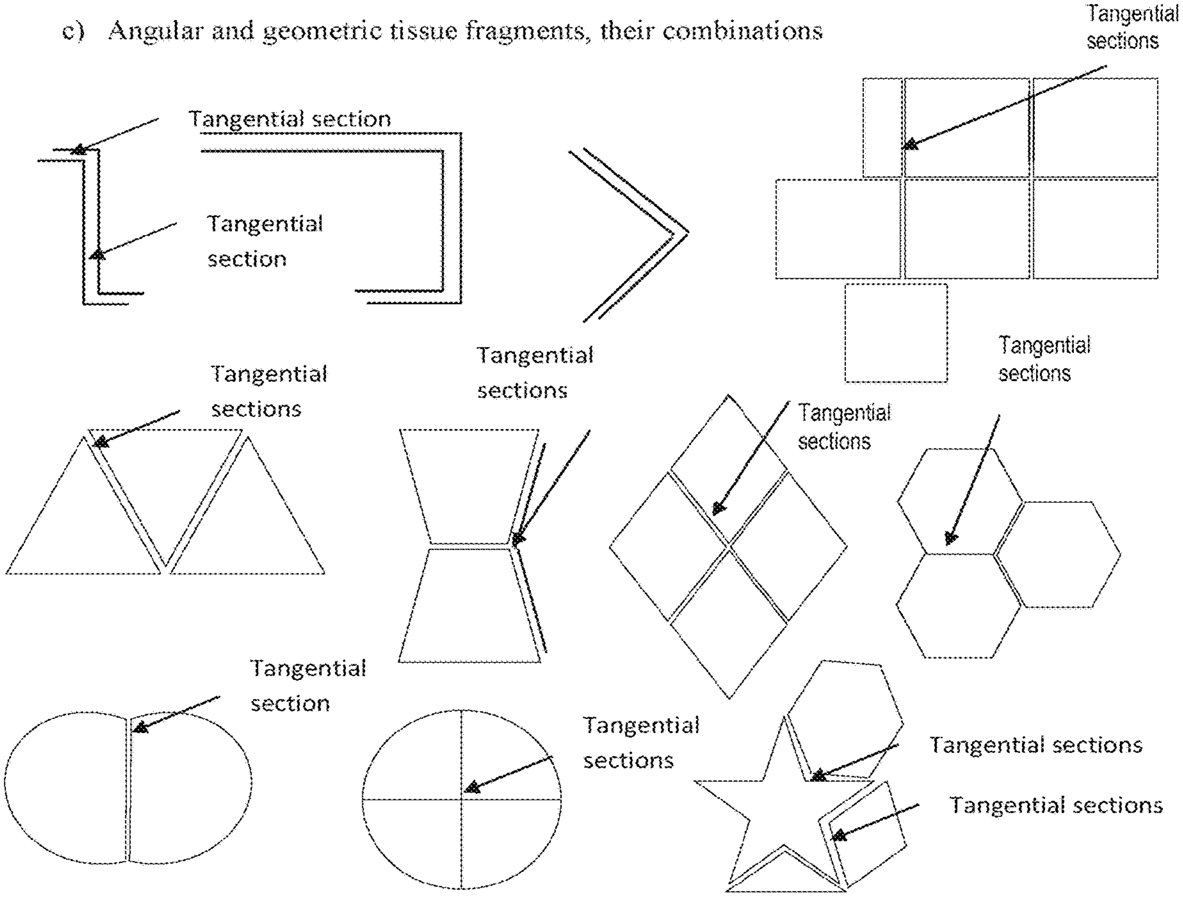

Heath, C.A. and Magari S.R., "Mini-review: Mechanical factors affecting cartilage regeneration in vitro", Biotechnology and Bioengineering, 1996, vol. 50, No. 4, pp. 430-437 (Abstract).
Wolf, F., et al. "Cartilage tissue engineering using pre-aggregated human articular chondrocytes", European Cells and Materials, 2008, vol. 16., pp. 92-99.
Polish Search Report issued Dec. 5, 2019 in connection with Polish Patent Application No. P.430801.
International Preliminary Report on Patentability issued on Feb. 8, 2022 in connection with PCT International Application No. PCT/EP2020/071826.
International Search Report issued by the International Searching Authority (ISA/O.E.P.M.) on Oct. 23, 2020 in connection with International Application No. PCT/EP2020/071826.
Feb. 11, 2021 Written Opinion issued in connection with PCT International Application No. PCT/EP2020/071826.
Hiemer, B., Genz, B., Jonitz-Heincke, A. et al. Devitalisation of human cartilage by high hydrostatic pressure treatment: Subsequent cultivation of chondrocytes and mesenchymal stem cells on the devitalised tissue. Sci Rep 6, 33747 (2016). https://doi.org/10.1038/srep33747.
Suto K, Urabe K, Naruse K, Uchida K, Matsuura T, Mikuni-Takagaki Y, Suto M, Nemoto N, Kamiya K, Itoman M. Repeated freeze-thaw cycles reduce the survival rate of osteocytes in bone-tendon constructs without affecting the mechanical properties of tendons. Cell Tissue Bank. Mar. 2012;13(1):71-80. doi: 10.1007/s10561-010-9234-0. Epub Nov. 30, 2010. PMID: 21116722; PMCID: PMC3286509.

* cited by examiner b) Arched sections c) Angular and geometric tissue fragments, their combinations

A

B

METHOD OF IN VITRO CHONDROCYTE AND CARTILAGE CULTURE TO OBTAIN MATERIAL FOR THE TREATMENT OF ARTICULAR CARTILAGE DEFECTS

RELATED APPLICATIONS

This application is a § 371 national stage of PCT International Application No. PCT/EP2020/071826, filed Aug. 3, 2020, claiming priority of Polish Patent Application No. P.430801, filed Aug. 2, 2019, the contents of each of which are hereby incorporated by reference into this application.

FIELD OF THE INVENTION

The present invention relates to a new method for treating human or animal tissue such as cartilage, particularly damaged tissue. More specifically, the invention relates to a method to obtain material for treating the damaged tissue, for example any cartilage damage, in particular as a result of traumatic or degenerative cartilage damage.

BACKGROUND OF THE INVENTION

Osteoarthritis (OA) is a degenerative joint disease characterized by joint pain and dysfunction due to the progressive and irreversible loss of articular cartilage. It is the fifth largest cause of disability in the US population, right after cardiovascular, cerebrovascular and respiratory diseases. The main OA risk factor for is age. There are also additional factors such as obesity, joint injuries, intense physical activity, e.g. competitive sports.

The number of diagnosed OA cases is still growing in many countries, e.g. in the USA in 1995-2005, there was an increase of about 6 million new cases (Lawrence R C, Felson D T, Helmick C G, et al. Estimates of the prevalence of arthritis and other rheumatic conditions in the United States. Part II. Arthritis Rheum. 2008; 58(1):26-35; Lawrence R C, Helmick C G, Arnett F C, et al. Estimates of the prevalence of arthritis and selected musculoskeletal disorders in the United States. Arthritis Rheum. 1998; 41:778-799). At the same time, there is a growing number of people suffering from degenerative and rheumatic diseases in the general population. By 2030, the number of diagnosed cases of degenerative disease in America is expected to reach 67 million, or 25% of the adult population, out of which 25 million or 9.3% of the adult population are to experience mobility limitations (Hootman J M, Helmick C G. Projections of U.S. prevalence of arthritis and associated activity limitations. Arthritis Rheum. 2006; 54:226-229). The result of these trends is an increase in the level of negative consequences in terms of the quality of life, as well as a huge increase in the healthcare system costs.

Almost every patient surgically treated for extensive degenerative joint lesions—especially regarding the knee, hip, shoulder and ankle joints—goes through a period when the destruction of cartilaginous joint surfaces is limited to a single site before progressing to generalized joint lesion. It is a source of a degenerative process slowly spreading over a joint. Along with the improvement of patient access to highly specialized diagnostic tools—such as MRI and arthroscopy—the time needed to detect inflammatory foci has been reduced. Currently, osteoarthritis is not diagnosed at the level of radiological changes visible on X-ray images—where they usually covered a significant part of the joint and required treatment with total joint prosthesis. However, due to the lack of proper tools for the treatment of small and medium articular cartilage damage, patients still cannot expect to avoid arthroplasty. Thus, the next stage of treatment is partial or surface arthroplasty, which, unfortunately, does not guarantee full recovery without having to repeat the surgery.

Total endoprosthesis still does not solve the problem of patient's mobility, physical fitness and does not prevent postoperative complications. The patient's physical capacity after endoprosthetic replacement is significantly reduced over a period of 3 months, patients rarely return to full capacity. The level of patient satisfaction measured by the degree of pain reduction and improvement of the operated limb function varies. The main postoperative problems of arthroplasty include the level of pain, limb function, and acceptance of the effects of the surgery itself. Joint excision means its definitive destruction—the next step can only be even more extensive tissue resection and implantation of an even larger implant—which usually leads to permanent disability after the second or third surgery.

One of the newly developed methods in joint therapy is the autologous chondrocyte implantation (ACI), which involves collecting a fragment of the patient's cartilage from an undamaged part of the joint, isolating the chondrocytes, multiplying them in vitro, and then implanting the cartilage cell suspension in the cartilage damage site.

However, the currently available methods do not allow obtaining tissue with proper structure and biological features that closely resemble natural tissue.

Available methods, including chondrocyte transplantation on collagen matrices, are associated with a long period of treatment and recovery. They are often burdened with a high failure rate of above 50%—due to the fact that the defect is not replaced with homogeneous tissue, but only partly with its components. The price of the procedures is very high. The therapeutic benefit-price ratio does not seem advantageous for the patient.

The known methods of in vitro chondrocyte culture for use in autologous transplants, i.e., cells propagation in culture and the administration of the suspension culture to the joint does not guarantee joint restoration and is associated with high cost and limited effectiveness compared to traditional surgical methods. Tissue reconstruction in vivo is difficult. Therefore, they are mainly applicable in the treatment of minor injuries. The present invention addresses the problems mentioned above.

The available chondrocyte cultures do not allow the propagated cells to transform into cartilaginous tissue. This is due to the difficulty in creating intercellular connections—this requires time, ideal conditions for cell nutrition, as well as mechanical restrictions.

For the reasons mentioned above, novel effective therapeutic solutions are sought. The present inventors have found efficient methods based on cell culture, more specifically in the field of transplantation of material obtained from cell culture, such as autologous chondrocyte transplantation. In particular the present invention provides a method for in vitro culture of chondrocytes, which can be used in the mentioned method of transplantation at an early stage disease an therefore, diminishes the risk of the requirement of surgery, postoperative complications are thus reduced, additionally the discovered methods represent a lower burden to the health care system in comparison to the prior art methods.

SUMMARY OF THE INVENTION

In a first aspect, the present invention provides a method of producing a cartilage tissue implant in vitro characterized by the following features:

i) providing at least a first and a second fragment of cartilage tissue, which each have at least one edge;
ii) placing the fragments in a culture medium in such that at least one edge of the first fragment is spaced ≤1 cm or less apart from at least one edge of the second fragment;
iii) adding a suspension of chondrocytes to the fragments; and
iv) cultivating the fragments and chondrocytes under cell culture conditions.

In a second aspect, the present invention relates to a tissue implant obtainable by the method of the first aspect for use in repairing tissue in a patient in need thereof.

In a third aspect, the present invention relates to a tissue implant obtainable by the method according of the first aspect for use in the treatment of damaged tissue of a patient with a disease.

LIST OF FIGURES

In the following, the content of the figures comprised in this specification is described. In this context please also refer to the detailed description of the invention above and/or below.

FIG. 1: Examples of preferred sections and arrangements. a) Rectilinear sections; b) Rectilinear sections c) Arched sections d) Angular and geometric tissue fragments, their combinations.

Figure 2:
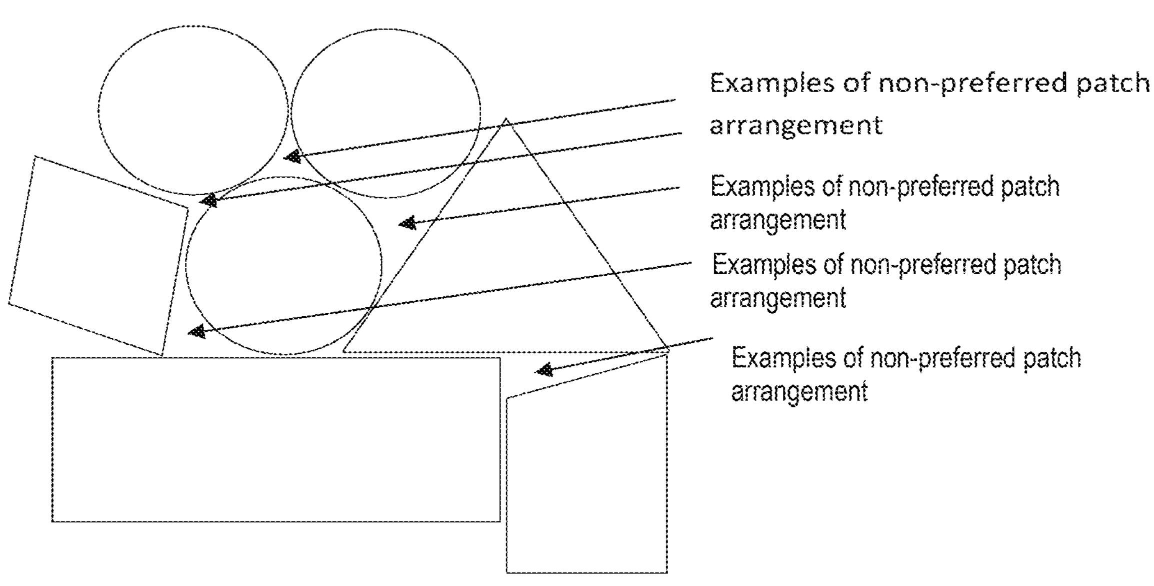

FIG. 2: Examples of non-preferred scrap arrangement—edges are not complementary along the entire length of tangential sections and there are large spaces between the edges of the tissue. Disadvantages: it is more difficult to fill the space and there is reduced mechanical resistance.

Figure 3:
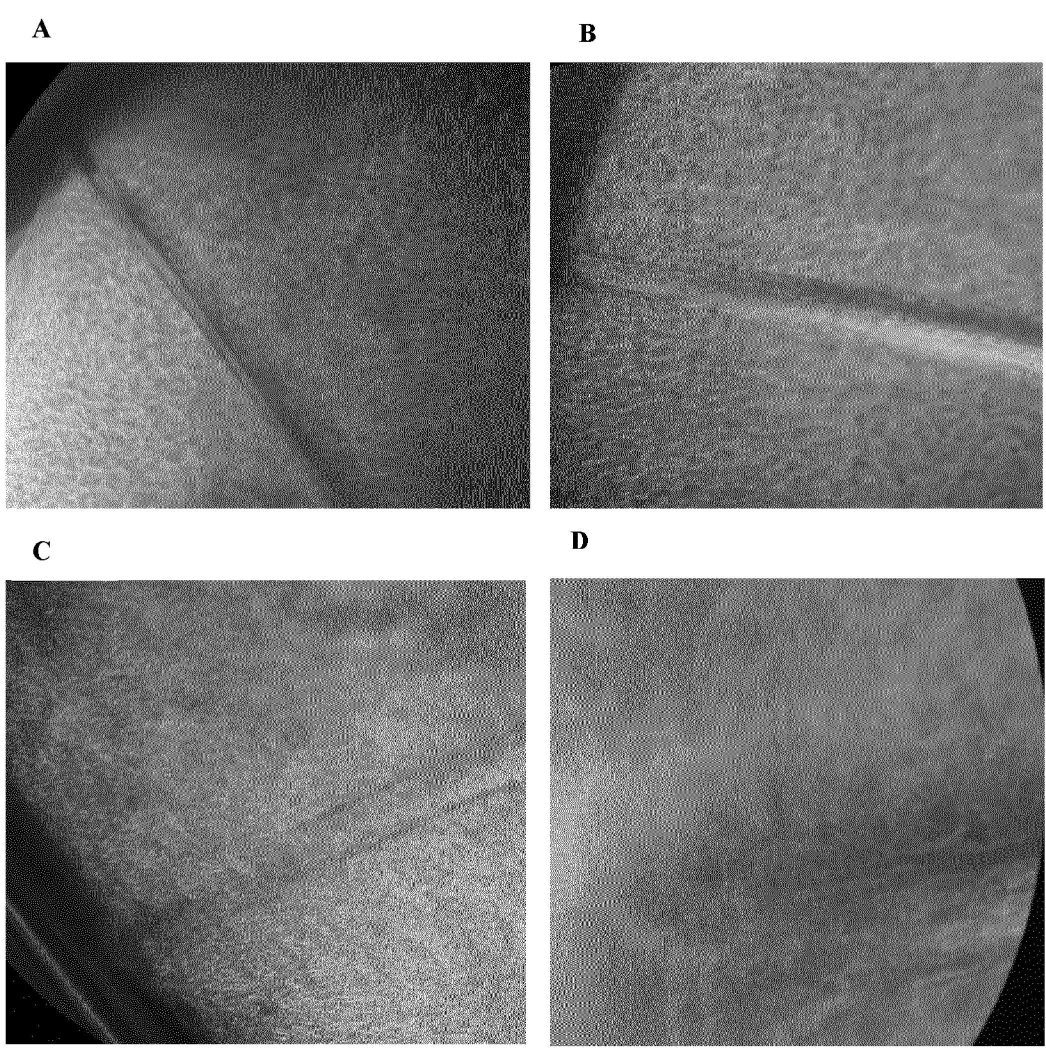

FIG. 3: Microscopic image of culture of tissue patches in medium 1. A microscopic image of tissue patches culture in medium 1 with 4.5 g/l glucose, 10% FBS, 2 mM glutamine-visualization of new tissue formation over time. A: Image of fragments of two tissue patches as closely adjacent to each other as possible along the tangential section of about 1 cm in length on the first day of culture (image documenting the culture baseline, day 1). Clearly visible free space between the contact surfaces of two tissue patches. B: Image of fragments of two tissue patches, adjacent to each other along the tangential section of about 1 cm and visible tissue filling, being formed between the contact surfaces of two tissue patches on the seventeenth day of culture in medium 1 with the addition of 4.5 g/l glucose, 10% FBS and 2 mM glutamine. C, D: Image of fragments of two tissue patches, adjacent to each other along the tangential section of about 1 cm and visible tissue filling, formed between the contact surfaces of two tissue patches on the fifty second day of culture in medium 1 with the addition of 4.5 g/l glucose, 10% FBS and 2 mM glutamine. The new tissue formed after fifty two days of culture clearly scars the free space at the junction of two tissue patches present on the first day of culture. Significant alignment of the old and new tissue colour at one end of the two contact surfaces of the tissue patch fragments is visible. Image taken using 10× magnification (A, B, C) and 40× magnification (D).

Figure 4:
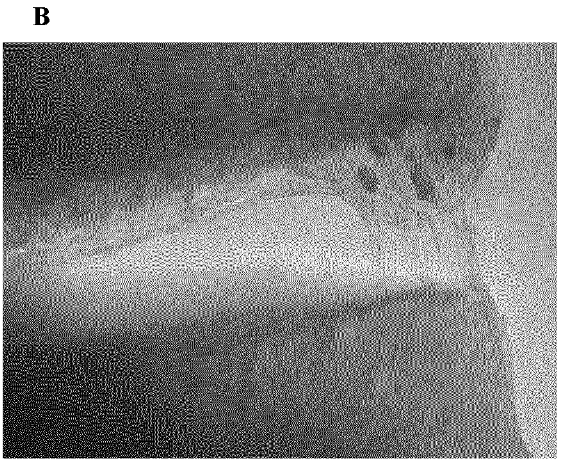

FIG. 4: Microscopic image of culture of tissue patches in mixture of medium 1 and medium 2. A microscopic image of tissue patches culture in a mixture of medium 1 and 2—visualization of the formation of new tissue connections over time. A: Image of fragments of two tissue patches as closely adjacent to each other as possible along a section of 0.6 cm in length on the first day of culture (image documenting the culture baseline). Clearly visible free space between the contact surfaces of two tissue patches. B: Image of fragments of two tissue patches, adjacent to each other along a section of about 0.6 cm and visible tissue connection, being formed between the contact surfaces of two tissue patches on the nineteenth day of culture in a mixture of medium 1 and medium 2 with the addition of 4.5 g/l glucose, 10% FBS, 2 mM glutamine and supplements: IGF-I and TGF at a concentration of 0.01%. New tissue is visible, both on the surface of one of the adjacent fragments and between the fragments of the tissue patches. The resulting connections have the nature of fibres connecting two contact surfaces with each other. Image taken using 10× magnification.

Figure 5:
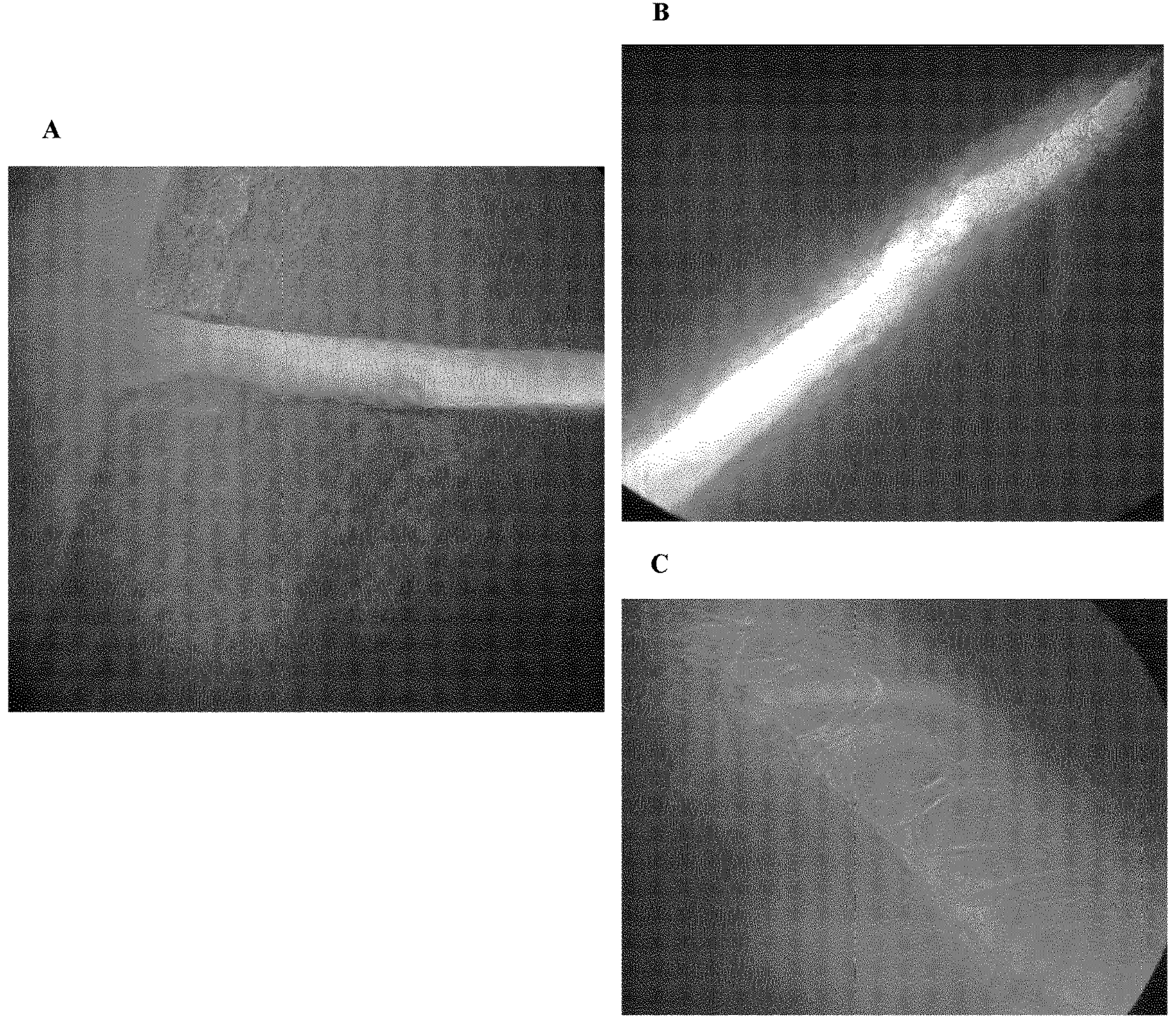

FIG. 5: Microscopic image of culture of tissue patches (patch $1^{st}$ and $2^{nd}$) in medium 1. A microscopic image of tissue patches culture (first and second) in medium 1—visualization of the formation of new tissue connections over time. A: Image of fragments of two tissue patches (first and second) as closely adjacent to each other as possible along a section of 1 cm in length on the first day of culture (image documenting the culture baseline). There is free space between the first tissue patch located closest to the edge of the plate and the next adjacent tissue patch. The first fragment was gently cut at the edge of the tangential surface to be identified in the subsequent stages of experiment (the first patch fragment is at the bottom of the image). B, C: Image of fragments of two tissue patches (first and second) and visible tissue connections formed between the contact surfaces, about 1 cm long, of two tissue patches on the twenty-seventh day of culture in medium 1 with the addition of 4.5 g/l glucose, 2% FBS, 2 mM glutamine and chondroitin at a concentration of 0.01%. Fibre-like connections form between the contact surfaces of the tissue patches. In the following days of culture, new tissue will form between them permanently binding two tissue patches. Connections of the same type were also observed between the second and third patches, and the third and fourth patches, respectively. Images [A, B] taken at 10× magnification, image [C] with 40× magnification.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland) and as described in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmacopeial Convention, Inc., Rockville Md., 2001.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

In the following, the elements of the present invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

DEFINITIONS

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise. As used herein "cell culture", or "cell culture conditions" refers to the process by which cells are grown under controlled conditions outside of their natural environment. Specifically, it refers to the growing of cells derived from multi-cellular eukaryotes, in particular animal cells (see also the definition of cells below). Typical growth conditions comprise temperatures between 35° C.-38° C., 3-7% $CO_2$, and a relative humidity of above 80%, preferably 90-99%. The cell culture of the present invention may comprise cells and tissue. The term "cell culture medium", "culture medium" or simply "medium" refers to a liquid or gel for supporting the survival or growth of cells and/or tissue, especially cells derived from multi-cellular eukaryotes, in particular animal cells and/or tissue. Such a medium comprises all nutrients required to support the survival or growth of such cells and/or tissue for at least 1, 2, 3, 4, 5, 6, 8, 9, 10, 11, 12, 13, 14, 15, 16, 17, 18, 19, 20, 21, 22, 23, 24, 25, 26, 27, 28, 29 or 30 days. The term "cell culture medium composition" refers to the ingredients the cell culture medium comprises. These ingredients are not necessarily all nutrients, but may serve other purposes, such as adjusting the cell culture conditions, e.g. the pH or osmolality, within a desired range. Furthermore, the ingredients are not necessarily all required to support the survival or growth of cells or production of recombinant proteins, but some may be dispensable, but nevertheless improve the medium supporting the survival or growth of cells or the production of recombinant proteins. The cell culture medium composition can be a dry powder composition, a liquid composition or a solid (e.g. gel or agar) composition. In a particular embodiment, the composition is sterile, i.e. it is free of all forms of life and/or infectious/replicating agents, such as fungi, bacteria, protozoa, parasites, viruses, aberrant proteins such as prions etc.

The medium of the cell culture may comprise a salt, amino acids, further components such as galactose, dextransulfate, spemidine, beta-glycerolphosphat and adenine; and a buffer. The salt may be selected from the group comprising calcium chloride, sodium phosphate, ammonium iron-(III)-citrate, magnesium sulfate, potassium chloride, sodium bicarbonate, sodium selenite, zinc sulfate, and sodium chloride. The amino acids may be selected from the group comprising arginine, asparagine, aspartic acid, cysteine, glutamic acid, histidine, hydroxyproline, isoleucin, leucine, lysine, methionine, penicillamine, phenylalanin, proline, serine, threonine, tryptophan, tyrosine, valine, alanine, aspartic acid, citrulline, cystine, glycine, and ornithine. The vitamins may be selected from the group comprising L-ascorbate, D-(+)biotine, D-calcium-panthothenate, choline chloride, folic acid, myo-inositol, nicotinamide, pyridoxine, riboflavin, thiamine, and vitamin B12. The further components may be selected from the group comprising dextrose, glutathione, hypoxanthine, lipoic acid, ethanolamine, uridine, spermine, pluronic F68, putrescine, thymidin, sodium pyruvate, galactose, dextransulfate, spermidine, beta-glycerolphosphat, and adenin. The buffer may be selected from the group comprising HEPES, MOPS, MES, BES, MOPSO, ACES, TAPS, Bicine, Tricine. Additionally, the medium may comprise growth factors, comprised for example in human and/or calf serum, preferably FBS. Alternatively, the medium may be free of serum.

The term "free of" refers to the medium being devoid of certain components, which are often ingredients of cell culture media of the art. Generally, it refers to the fact that these components have not been willfully made part of the composition and it includes the possibility of contaminations, for example due to handling the medium, its containers or tools for handling the medium or its containers. Particularly, it excludes all measurable traces of these components, measured for example by state of the art methods such as chromatography, in particular High-Performance Liquid Chromatography (HPLC).

The term "serum" refers to a blood fraction that contains electrolytes, antibodies, antigens, hormones and exogenous substances as well as all other substances comprised in blood, except blood cells, clotting factors and all other proteins involved in blood clotting or coagulation (provided they form part of the blood clot). In particular, the term refers to serum usually used for cell culture applications, such as cow, chicken, goat, human, sheep, pig or rabbit sera. In particular, the term refers to an undefined (in as far as its composition and/or the concentrations of its components are not defined or known) cell culture component. As such, its exclusion does not exclude any components of the medium composition of the invention, especially as specified herein, even though serum may contain one or more of these components.

As used herein "monolayer culture", is a type of culture wherein cells are grown in a single layer on a flask or Petri dish containing the culture medium. A "suspension culture is a type of culture wherein cells are maintained in suspension in the culture medium so that they are distributed evenly within it. The term "protein" refers to biological molecules comprising one or more polypeptides. A polypeptide is a single linear polymer chain of amino acids linked by peptide bonds, for example of a length of at least 50, 60, 70, 80, 90 or 100 amino acids.

As used herein, "treat", "treating", "treatment" or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s).

As used herein the "cell" or "tissue" may be an animal or human cell or tissue. An animal cell or tissue may be a cell or tissue of a primate, mouse, rat, rabbit, dog, cat, hamster, cow, insect etc. The cell may be a suspension or an adherent cell. A suspension cell is a cell that may naturally live in suspension (i.e. without being attached to a surface), or a cell that has been modified to be able to survive in suspension cultures, for example to be grown to higher densities than adherent conditions would allow. An adherent cell is a cell that requires a surface, such as tissue culture plastic or a microcarrier, which may be coated with extracellular matrix components (such as collagen and laminin) to increase adhesion properties and provide other signals needed for growth and differentiation. In one embodiment, the adherent cell is a monolayer cell. For example, the cell is selected from the group consisting of a chondrocyte cell, a hybridoma cell, a primary epithelial cell, an endothelial cell, a keratinocyte, a monocyte/macrophage, a lymphocyte, a hematopoietic stem cell, a fibroblast, and a hepatocyte. More specifically, it may be a chondrocyte cell selected from the group consisting of heterologous, homologous and autologous chondrocytes. In particular, it is an autologous chondrocyte cell. In particular the tissue is cartilage tissue, more specifically, hyaline cartilage tissue.

As used herein a "tissue fragment" is a piece of tissue. In the context of the present invention tissue fragments that are "complementary" in shape to each other refers to fragments which can be put together in a lock and key similar way, or in other words like puzzle pieces because of their shape. A "complementary" shape is meant as edges of the tissue fragments which are parallel running and therefore fit particularly well together.

As used herein an "implant" or "tissue implant" is a biomedical tissue used for organ transplantation. It is produced to replace a missing biological structure, support a damaged biological structure, or enhance an existing biological structure. The surface of the implants that contact the body might be made of a biomedical material such as titanium, silicone, or apatite. In one embodiment of the invention the tissue implant is made of the tissue obtained by the cultivation of cells with tissue, wherein the cells are preferably chondrocytes and the tissue is preferably cartilage.

Aspects of the Invention and Preferred Embodiments

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In the work leading to the present invention, it was surprisingly shown that a tissue implant can be produced by an in vitro method, which comprises culture of cartilage and chondrocytes, which can be effectively used in a method of transplantation at an early stage disease an therefore, diminishes the risk of the requirement of surgery, postoperative complications are thus reduced, additionally the discovered methods represent a lower burden to the health care system in comparison to the prior art methods. In a first aspect, the present invention provides a method for producing a cartilage tissue implant in vitro, characterized by the following features:

i) providing at least a first and a second fragment of cartilage tissue, which each have at least one edge;
ii) placing the fragments in a culture medium in such that at least one edge of the first fragment is spaced ≤1 cm or less apart from at least one edge of the second fragment;
iii) adding a suspension of chondrocytes to the fragments; and
iv) cultivating the fragments and chondrocytes under cell culture conditions.

The term "edge" with reference to the fragment of cartilage tissue refers to the outside limit of the fragment of cartilage tissue. The edge may be the natural outside limit of the cartilage tissue or it may be the result of cutting isolated cartilage tissue, e.g. with a scalpel, in this case the edge is an artificial edge. Since the edge runs around the entire cartilage fragment, the edge may be of natural origin for its entire length (in this case the "fragment" is not really a fragment but a piece of cartilage tissue as it naturally occurs. Alternatively, the edge may be partially of natural origin and partial of artificial origin or it may be entirely artificial. The latter is the case, if the fragment of cartilage is cut out from a larger piece of cartilage tissue. This may be the case, if the fragment is cut out from a larger piece of cartilage tissue during a surgical procedure or a larger piece of cartilage may be cut into two or more fragments after surgical removal. The cartilage tissue may be removed from the patient that is subsequently treated, (autologous cartilage) or it may be from a different person—a donor—(heterologous cartilage). Thus, the term "edge" is used in the context of the present invention to also refer to a part of the edge of the fragment of the cartilage tissue. Preferably, the part of the edges of the two fragments that are placed in vicinity of each other have corresponding shapes, e.g. the parts of both edges are straight or one is inwardly curved and the other outwardly curved.

As noted above the term "fragment of cartilage tissue" may refer to a piece of cartilage tissue as it naturally occurs or to one that has been cut to a smaller size than naturally occurring. The fragment of cartilage may have its natural thickness, preferably between 0.01 mm to 10 mm, more preferably between 0.1 to 6 mm. In some instances it may be preferable to cut thinner slices of cartilage from a thicker piece of naturally occurring cartilage tissue. Such fragments of cartilage preferably have a thickness between 0.1 mm to 5 mm, more preferably between 0.1 to 4 mm, more preferably 1 to 3 mm. Is it further preferred that the thickness of the fragment is essentially uniform over the entirety of the fragment.

Preferred sources of cartilage that may be used in the method of the present invention are heterologous or autologous sources, preferably autologous. Preferably the source is any joint, more preferably the damaged joint to the treated. Preferably wherein the tissue source is a healthy tissue source In step ii) the space between the at least one edge of the first fragment and the at least one edge of the second fragment is 0.9 cm, 0.8 cm, 0.7 cm, 0.6 cm, 0.5 cm, 0.4 cm, 0.3 cm, 0.2 cm, 0.1 cm. Preferably the space is ≤0.5 cm, preferably ≤0.1 cm, preferably there is no space.

In step iii) the chondrocytes are heterologous, homologous or autologous chondrocytes. Preferably the chondrocytes are autologous chondrocytes.

In a preferred embodiment of the first aspect, the edges of the fragments, preferably if they are in contact with each other, are in contact along a tangential section, preferably in one of the arrangements as show in FIG. 1. Preferably, the tangential section of contact has a length of at least 0.1 cm, more preferably of at least 0.5 cm, more preferably at least 1 cm.

In a preferred embodiment at least three, more preferably at least four, at least five or at least six fragments are spaced apart as indicated above for the first and second fragment. In this way a larger cartilage sheet can be generated from several fragments.

In a preferred embodiment the medium comprises one or more salts, amino acids, further components such as galactose, dextransulfate, spemidine, beta-glycerolphosphat and adenine; and a buffer.

The salt may be selected from the group comprising calcium chloride, sodium phosphate, ammonium iron-(III)-citrate, magnesium sulfate, potassium chloride, sodium bicarbonate, sodium selenite, zinc sulfate, and sodium chloride.

The amino acids may be selected from the group comprising arginine, asparagine, aspartic acid, cysteine, glutamic acid, histidine, hydroxyproline, isoleucin, leucine, lysine, methionine, penicillamine, phenylalanin, proline, serine, threonine, tryptophan, tyrosine, valine, alanine, aspartic acid, citrulline, cystine, glycine, and ornithine.

The vitamins may be selected from the group comprising L-ascorbate, D-(+)biotine, D-calcium-panthothenate, choline chloride, folic acid, myo-inositol, nicotinamide, pyridoxine, riboflavin, thiamine, and vitamin B12.

The further components may be selected from the group comprising dextrose, glutathione, hypoxanthine, lipoic acid, ethanolamine, uridine, spermine, pluronic F68, putrescine, thymidin, sodium pyruvate, galactose, dextransulfate, spermidine, beta-glycerolphosphat, and adenin.

The buffer may be selected from the group comprising HEPES, MOPS, MES, BES, MOPSO, ACES, TAPS, Bicine, and Tricine.

Additionally, the medium may comprise growth factors, comprised for example in human and/or calf serum, preferably FBS. Alternatively, the medium may be free of serum. In a preferred embodiment the medium further comprises insulin growth factor (IGF), and/or transforming growth factor (TGF), and optionally chondroitin and/or insulin. Preferably the medium comprises at least 0.01 wt % IGF, and/or at least 0.01 wt % TGF, and optionally at least 0.01 wt % chondroitin and/or at least 0.1 wt % insulin. Preferably the medium comprises at least 0.01 wt % IGF, at least 0.01 wt % TGF, at least of 0.01 wt % chondroitin and at least 0.1 wt % insulin.

In a preferred embodiment the fragments are cultured in the culture medium for at least 14 days after step (ii) before adding the suspension of chondrocytes in step (iii). Preferably the fragments are cultured for 14-18 days, preferably 18-25 days, preferably 25-30 days, preferably 30-42 days and up to at least five months.

In a preferred embodiment the chondrocytes are added to the culture medium in step (iii) of the method of the first aspect to a final concentration of at least 4,000, preferably 4,000 to 0,000, preferably 10,000 to 40,000, preferably 16,000 to 40,000 chondrocytes per ml of culture medium. Preferably the final concentration of the chondrocytes added to the culture medium in step (iii) of the method of the first aspect is 16,000 chondrocytes per ml of culture medium.

In a preferred embodiment the suspension of chondrocytes is obtained by enzymatic digestion, preferably by digestion with a protease. Preferably, the enzymatic digestion is performed with collagenase, trypsin, hyaluronidase, and/or tosyllysylchloromethane, more preferably with collagenase, and even more preferably with collagenase II.

In a preferred embodiment the suspension of chondrocytes are cultured in an adherent monolayer prior to being suspended. Preferably, the cultivation temperature is between 35-38° C. and/or $CO_2$ concentration is between 4-6%, more preferably the temperature is 37° C. and the $CO_2$ concentration is 5%.

In a preferred embodiment one edge of the first fragment is complementary to one edge of the second fragment, for example one edge of the first fragment fits into one edge of the second fragment similar to a lock and key model. The shape of the fragments may be oval, round, square, rectangular or bulky, preferably the shape is oval. The shape of at least one edge of the fragments may be curved or straight, preferably straight.

In a second aspect the present invention provides a tissue implant obtainable by the method according to the first aspect of the invention for use in repairing tissue in a patient in need thereof, preferably wherein the tissue to be repaired is damaged tissue, more preferably damaged cartilage tissue.

In a third aspect the present invention provides a tissue implant obtainable by the method according to the first aspect of the invention for use in the treatment of damaged tissue of a patient with a disease. Preferably the disease comprises joint diseases, such as osteoarthritis, rheumatoid arthritis, spondyloarthritis, juvenile idiopathic arthritis lupus, gout, and bursitis. Preferably the disease is osteoarthritis.

In a preferred embodiment the treatment comprises the implantation of the tissue implant in the defect site. In other words, in result of experimental research, a method of hyaline cartilage cell culture was developed to obtain material for the treatment of cartilage conditions. A method was developed, involving the simultaneous use of native tissue fragments for culture, which are combined in vitro into larger pieces and chondrocyte suspensions, which act as an adhesive to connect tissue fragments.

Therefore, properly planned experimental studies were carried out to develop methodology for conducting chondrocyte culture and, among other things, various cell densities, lengths of contact surfaces of connected fragments, various types of supplements and culture media were tested to create intercellular connections that are not easily violated.

According to the invention, the cells grow and divide while being adhered to the surface of the culture medium e.g. plates. They are in suspension only when they are peeled off from the surface to the passage and when suspended in the medium, they are used to flood the tissue.

The invention relates to methodology that allows in vitro culture of cells and tissue fragments so that it is possible to obtain cartilaginous tissue in a near-natural form rather than a suspension of cells or cells placed in a matrix, as known from the present state of the art. Cultivation of cells and fragments of hyaline cartilage is carried out in vitro and the obtained material in the form of tissue is implanted in the defect site. The invention consists in collecting smaller fragments of normal cartilage tissue from less or not loaded places in the patient's joint, and then placing them in a medium suitable for cell/tissue culture, where, during culturing, smaller fragments are combined into patches with a larger surface by directly placing at least two, preferably at least three to ten, tissue fragments—pieces in close proximity, i.e. so that at least one edge of each fragment is in contact with another. The parallel edges of at least two, preferably at least three to ten, fragments of tissue are matched according to their shape so that the patches can be connected by joining the matched edges together along the contacting section, where fragments or the entire edges are arranged in a parallel manner.

According to the invention, the method of conducting in vitro chondrocyte culture to obtain material for the treatment of articular cartilage defects consists of cutting the obtained hyaline cartilage into at least two tissue fragments and placing these fragments on a culture plate next to each other in culture medium containing at least 2 mM glutamine, at least 2% FBS, at least 4.5 g/l glucose, with the matched shape of the tissue fragments at least along one section of the edge of each fragment so that after the fragments are arranged closely the space between at least two tissue fragments is as small as possible and so that the area of the culture plate filled with tissue fragments is as small as possible. The edges are adjusted in such a way that, during culture, fragments are joined together at least along one section in contact with another. Chondrocyte suspensions are added to the culture and tissue fragments with chondrocytes are cultured. The culture medium is changed in a set time period by adding chondrocytes to the culture medium and the cells are cultured until the tissue fragment is joined to at least a part of a section in contact with another. Preferably, the tangential section between at least two joined tissue fragments is minimum 0.1 cm, most preferably at least 0.5 cm. Preferably, the tissue fragments should have an oval-like shape. Preferably, the shape of the tissue fragments is selected so that the tissue fragments in culture adhere very closely to each other along the tangential section.

Preferably, the culture medium contains supplements at a concentration of minimum 0.01% IGF and/or 0.01% TGF and/or 0.01% chondroitin and/or a minimum of 0.1% insulin. Preferably, the culture medium contains 55-75 mg/l sodium pyruvate and sodium bicarbonate, 2 mM-4 mM glutamine, 2%-10% FBS, and at least 4.5 g/l glucose as well as ethanolamine and/or glutathione and/or ascorbic acid and/or insulin and/or transferrin and/or copper sulphate and/or manganese chloride.

Preferably, before the addition of chondrocytes, the tissue fragments themselves are cultured in the medium, preferably for at least 14 days, after which the chondrocytes are added to the culture. Preferably, chondrocyte suspensions are added to the tissue fragments in such an amount that at least 40,000 chondrocytes are present per 2.5 ml of culture medium. Preferably, the minimum chondrocyte concentration for culturing two fragments with a tangential segment length of 0.1 cm-1 cm is 40,000 chondrocytes per 2.5 ml medium.

Preferably, cultured chondrocytes are obtained by enzymatic digestion, after which the required number of cells is obtained by culturing chondrocytes in monolayer in adherent culture. Preferably, the cells are cultured in 37° C. and 5% CO2.

During experimental research, it was established that the minimum tangential section along the joined edges, i.e. the tangential section, must be minimum 0.1 cm long; the edges can be brought closer together along a parallel section. The tangential section may be a fragment of the edge of tissue patch or the entire edge of tissue patch. The edges to be joined should be straight or rounded. During the culture, patches are combined using chondrocyte suspension culture obtained from the tissue of the same donor. Cartilage contains both chondrocytes and extracellular matrix. It is important to select the shape of the tissue fragments—patches so that the space between the joined edges of the cartilage fragments is as small as possible—the edges or edge fragments should contact each other along at least a 0.1 cm long section. Matching the shapes of the tangential edges of the patches—tissue fragments should take place, at the latest, at the stage of placing them in the immediate vicinity of the culture plate, before adding the chondrocytes.

Thanks to this, culture allows obtaining hyaline cartilage, not just cells. At the junction of cultured tissue patches, the obtained tissue may be characterized with weaker mechanical strength or less mature, but it will be tissue with a solid structure provided by intercellular junction.

According to the invention, the procedure includes:

1. Collection of hyaline cartilage from the patient
2. Cutting the tissue into appropriate patches—fragments
3. Subjecting some patches to enzymatic digestion to obtain chondrocytes and establishing cell culture—chondrocyte culture
4. Placing the remaining patches (not digested) in the culture medium—culture of tissue fragments to which chondrocytes are added
5. After obtaining the right amount of chondrocytes in the culture, cells are obtained for further use in combined culture of tissue and cell fragments, while the cells allow the connection of non-digested tissue patches
6. Chondrocytes in suspension are added to the culture plate with the tissue fragments.

Suspension cells will locate themselves in the fissure and assist the fusion of minimum two edges of at least two tissue fragments, and/or the cells will adhere to the cell culture plate and proliferate and release factors which promote fusion of the cartilage fragments with each other.

In the combined culture, the undigested patches—tissue fragments of the culture are placed close to each other adjusting the shape of the edges along the tangential section, so that the space between the joined edges is as small as possible, i.e. the tangential edges of the tissue fragments can be joined.

It is important to select the shape of the fragments—tangential edges so that the space between the edges of the fragments of cartilage in contact with each other is as small as possible. Matching the shapes of the tangential edges should take place, at the latest, at the stage of placing them in the immediate vicinity of the culture plate, before adding the suspended chondrocytes.

The invention was developed as a result of long-term experimental research. Examples 1-3 show attempts of culturing cells to obtain hyaline cartilage material for reconstruction of damaged articular cartilage.

The invention is demonstrated using examples of preparation and drawings. FIG. 1 shows the principle of joining tissue fragments—A-B—tangential sections, C-shapes of tissue fragments. FIG. 2 shows the principle of joining tissue fragments—incorrect shapes of tissue fragments. FIGS. 3-5—microscopic images.

Examples of connections that are not preferred are all types of arc-linear as well as geometric connections with differing angles, where the space between the fragments is relatively large and there are no tangential sections with at least a 0.1 cm long edge of a patch being parallel to the other. They are shown in FIG. 2. FIG. 2 shows examples of non-preferred scrap arrangement—edges are not complementary along the entire length of tangential sections and there are large spaces between the edges. Disadvantages: it is more difficult to fill the space and there is reduced mechanical resistance.

EXAMPLES

Example 1—Attempt to Culture Only Hyaline Cartilage Tissue Fragments According to the Invention In order to create a uniform flap of cartilage tissue using in vitro method to obtain material for the treatment of articular cartilage defects. First, clinical material was obtained from an adult human in the form of a hyaline cartilage tissue fragment collected from the least load bearing parts of the knee joint. Tissue is collected from the patient from places with low physical load. This tissue should be healthy. The shape of the collected flap or flaps of cartilage may therefore be different. One or more cartilage fragments can be collected. One or several fragments can be divided into smaller ones by cutting them across or along the cartilage—bone line. Next, in the case of collecting a large fragment of articular cartilage, it was cut into smaller fragments under sterile conditions.

Immediately after collecting the material from the patient, it was transferred to a sterile 50 ml tube filled with physiological saline solution (0.90% NaCl) so that the tissue was completely immersed in the solution. Then the cartilage was cut to thin, maximum 3 mm thick slices, of various shapes and sizes below 1 cm in length or width or thickness.

The obtained tissue fragments, completely immersed in physiological saline (0.90% NaCl), were transported in a sterile 50 ml tube to a cell culture laboratory. Tissue transport was carried out under sterile conditions at 2-8° C. All operations performed with tissues were carried out under laminar flow conditions. After preparing the right size patches, the resulting material served as the starting base for obtaining the final tissue flap.

The final tissue flap patch for the treatment of articular cartilage defects was to be formed on a matrix of tissue slices properly arranged relative to each other on the surface of the culture plate, cultured in appropriate conditions and culture medium composition.

An important step was to properly adjust the shape of the tangential edges of the tissue slices. By joining the tissue fragments along the tangential edges, the tissue fragments were as close to each other as possible on the culture plate.

A culture trial was performed using 2-4 tissue fragments in contact with one another along at least one straight-lined section—the tangential edge of 0.1-1 cm in length.

As described earlier, the shape was matched according to the tangential edges of at least two tissue fragments—patches—joined edges. The maximum length/width as well as the maximum number of fragments—patches depended on the size of the culture plate.

Out of all the collected tissue patches, it was necessary to select at least two up to as many patches as would fit on the surface of a well of the culture plate. If the aforementioned already prepared patch system was not possible to use due to the mismatch of the adjacent patch edges, they were cut and given the desired shapes after collecting the material from the patient.

It was assumed that at these stages of tissue culture, where a new tissue fragment formation was planned, based on previously collected and prepared tissue fragments, it was crucial to place a minimum of two tissue fragments next to each other. These fragments should be arranged in such a way that the joined fragments have tangential edges being as long as possible and compatible in shape with the adjacent fragment/fragments, so that the filled space of the culture plate is as small as possible. This effect can be achieved both at the stage of tissue collection from the patient by collecting fragments of the appropriate shape, as well as later in the laboratory in vitro. Edge shape compatibility—their location next to each other being such that at least one edge of one tissue fragment contacts the edge of the other, which ensures easier filling of the area between them by chondrocyte suspension thanks to minimizing the volume of free space between cartilage fragments, as well as increasing mechanical resistance of the newly obtained tissue fragment at the junction site.

During culture, it was observed whether the tissue flaps—patches—would increase their area and whether the spaces between the edges would be filled. Compatible tissue patches slices of approximately 1 mm×1.2 cm×0.7 cm were transferred to wells of a 6-well sterile cell culture plate filled with 2.5 ml cell culture medium 2 containing: calcium anhydrous chloride, sulphate copper pentahydrate, ferrous sulphate heptahydrate, magnesium chloride, potassium chloride, sodium bicarbonate, sodium chloride, anhydrous dibasic sodium phosphate, zinc sulphate heptahydrate, L-Alanine, L-arginine hydrochloride, L-asparagine monohydrate, L-aspartic acid L-cysteine hydrochloride, L-glutamic acid, L-Glutamine, glycine, L-Histidine trihydrochloride monohydrate, L-isoleucine, L-Leucine, L-lysine hydrochloride, L-methionine, L-phenylalanine, L-Proline, L-Serine, L-threonine, L-Tryptophan, L-tyrosine dibasic dihydrate, L-valine, D-biotin, choline chloride, folic acid, myo-inositol, niacinamide, D-pantothenic acid (hemicalcium), pyridoxine hydrochloride, riboflavin, thiamine hydrochloride, vitamin B12, D-glucans Ozone, hypoxanthine, linoleic acid, phenolic red, putrescine hydrochloride, monosodium pyruvic acid, thymidine with the addition of a 1-fold concentrated Glutamax supplement solution. The cells were cultured in 37° C. and 5% CO2 for 7 days. Junctions between two tissue fragments, their viability and proliferation were monitored using 10× and 40× optical magnification. Tissue modifications: connection, viability and proliferation were observed regularly, before each subsequent passage and medium replacement, using an inverted optical microscope at 10× and 40× magnification. Culture medium and supplements were replaced once a week.

Each subsequent medium replacement involved:

1) removing the old medium
2) gentle transfer of tissue patches slices to a new culture plate
3) addition of fresh medium.

During culture, it was observed whether the tissue flaps—patches—would increase the area and whether the spaces between the edges would be filled. After five months of culture of the tissue fragments alone—without chondrocyte suspension, proceeding according to the invention, no connections were observed between pairs of cartilage tissue fragments placed in one well. There was also no new tissue growing on the surface of the old tissue.

Example 2—Attempt to Culture Only Cartilage Tissue Fragments According to the Invention The culturing procedure was similar to that described in example 1.

Compatible tissue patches were transferred to the wells of a 6-well sterile cell culture plate filled with 2.5 ml cell culture medium 2 with the addition of a 1-fold concentrated solution of Glutamax supplement and glucose [4.5 g/l].

After five months of culture, no connections were observed between pairs of cartilage tissue fragments placed in one well. There was also no new tissue growing on the surface of the old tissue.

Example 3—Attempt to Culture Only Cartilage Tissue Fragments According to the Invention The culture procedure was carried out as described in example 1, except that compatible tissue slices were transferred to a 6-well sterile cell culture plate filled with 2.5 ml cell culture medium 1 containing: anhydrous calcium chloride, iron nitrate, potassium nitrate chloride, magnesium sulphate anhydrous, sodium chloride, sodium bicarbonate, potassium phosphate monobasic monohydrate, D-glucose, L-arginine hydrochloride, L-cystine dihydrochloride, L-glutamine, glycine, L-histidine hydrochloride monohydrate, L-isoleucine, L-leucine, L-lysine hydrochloride, L-methionine, L-phenylalanine, L-serine, L-threonine, L-tryptophan, disodium L-tyrosine dihydrate, L-valine, calcium D-pantothenate, choline chloride, folic acid, and-inositol, niacinamide, riboflavin, thiamine hydrochloride, pyridoxine hydrochloride) with 4-(2-hydroxyethyl) piperazine-1-ethanesulfonic acid sodium salt with high glucose concentration [4.5 g/l].

After five months of culture, no connections were observed between pairs of cartilage tissue fragments placed in one well. There was also no new tissue growing on the surface of the old tissue.

Example 4—General Description of the Method According to the Invention

In order to create a uniform flap of cartilage tissue using in vitro method to obtain material for the treatment of articular cartilage defects. First, clinical material was obtained from an adult human in the form of a hyaline cartilage tissue fragment collected from the knee joint. Hyaline cartilage should preferably be collected from the treated joint (it can be knee, hip, ankle, shoulder or any other joint). It can be collected from another joint when the treated joint is small or difficult to extract hyaline cartilage. It should always be the least load bearing site. Tissue is collected from the patient from places with low physical load. This tissue should be healthy. The shape of the collected flap or flaps of cartilage may therefore be different. One or more cartilage fragments can be collected. One or several fragments can be divided into smaller ones by cutting them across or along the cartilage—bone line.

Next, in the case of collecting a large fragment of articular cartilage, it was cut into smaller fragments under sterile conditions.

Immediately after collecting the material from the patient, it was transferred to a sterile 50 ml tube filled with physiological saline solution (0.90% NaCl) so that the tissue was completely immersed in the solution. Then the cartilage was cut to thin, maximum 3 mm patches of various shapes and sizes below 1 cm in length/width (this applies to both fragments that will form the basis for obtaining the final tissue patch and fragments that will give rise to the culture of free chondrocytes).

The preferred thickness/length/width of the fragments: 1 mm×0.5 cm×0.5 cm, 1 mm×0.6 cm×0.6 cm, 1 mm×0.7 cm 0.7 cm, 1 mm×0.8 cmx 0.8 cm, 1 mm×0.9 cm×0.9 cm, 1 mm×1 cm×1 cm, 2 mm×1 cm×1 cm, 3 mm×1 cm×1 cm. The resulting tissue fragments of approximately 1 mm×1 cm×1 cm, completely immersed in physiological saline (0.90% NaCl), were transported in a sterile 50 ml tube to a cell culture laboratory. Tissue transport was carried out under sterile conditions in 2-8° C.

The dimensions and shape of the joined flaps patches do not matter. It is important to prepare them so that the space between the joined edges along the tangential section of at least two tissue fragments is as small as possible, so that the edges are joined along at least 0.1 cm of the tangential section length. The size of the fragment itself also depends on the size and shape of the injury as well as the size and shape of healthy cartilage collected to obtain the "biological prosthesis" in the form of the reconstituted fragment of cartilage tissue according to the invention. The tangential section was at least 0.1 cm long. All operations carried out using tissue or cells were carried out under laminar flow conditions. After preparing patches of suitable size, all fragments were divided into two parts. One of them was used to obtain chondrocyte suspension, i.e. a mixture that serves as tissue building material in cell culture with tissue fragments. The other constituted fragments for culturing tissue flaps patches and constituted the basis for obtaining the final flap of reconstituted tissue.

The final tissue flap patch for the treatment of articular cartilage defects was obtained according to the procedure described below, i.e. tissue slices of a fixed shape, arranged relative to each other on the surface of the well of the culture plate were combined using chondrocyte suspension—in "tissue-cell" culture.

1) Preparation of Cartilage Tissue Fragments for Further Culture of Tissue Fragments.

An important stage is the proper selection of these tissue patches whose edges will allow them to be positioned as close to each other as possible on the culture plate. Tissue fragments must be in contact with each other along at least one rectilinear segment. There must be at least 2 tissue fragments. Minimum length of a tissue fragment of any shape: minimum: 0.1 cm, preferably at least 0.5 cm. Minimum width of a tissue fragment of any shape: at least: 0.1 cm, preferably at least 0.5 cm. Tissue thickness: at least 1 mm and 4 mm or less.

As described earlier, the shape is matched according to the tangential edges of at least two tissue fragments—patches—joined edges along the tangential section. This length of the tangential section of the joined edges should be at least 0.1 cm in length, preferably minimum 0.5 cm in length regardless of whether the section is rectilinear or curved because this length refers to the tangential line—the tangential section and not straight line. The maximum length/width as well as the maximum number of fragments—patches depends on the size of the culture plate and the therapeutic objective.

Out of all the collected tissue patches, it was necessary to select at least two up to as many patches as would fit on the surface of a well of the culture plate. If the aforementioned already prepared patch system was not possible to use due to the mismatch of the adjacent patch edges, they were cut and given the desired shapes after collecting the material from the patient.

At these stages of tissue culture, where a new tissue fragment formation was planned, based on previously collected and prepared tissue fragments, it was crucial to place a minimum of two tissue fragments next to each other. These fragments should be arranged in such a way that the joined fragments have tangential edges being as long as possible, at least 0.1 cm, and compatible in shape with the adjacent fragment/fragments to minimise the free space between the cartilage fragments so that the filled space of the culture plate is as small as possible. This effect can be achieved both at the stage of tissue collection from the patient by collecting fragments of the appropriate shape, as well as later in the laboratory in vitro. Edge shape compatibility—their location next to each other being such that at least one edge, or its section, of one tissue fragment contacts the edge of the other tissue fragment, which ensures easier filling of the area between them by chondrocyte suspension thanks to minimizing the volume of free space between cartilage fragments, as well as increasing mechanical resistance of the newly obtained tissue fragment at the junction site. Possible examples of edge shapes and ways of joining them are shown in FIG. 1, examples do not exhaust the list of all possibilities. During culture, it is important to obtain and connect a minimum of two tissue fragments directly adjacent to each other along a section of adjacent edges, where the minimum tangential section length is 0.1 cm in the case of both straight and curved sections. This value applies to the length of the tangential segment of the fragment or the entire edge of the tissue fragment regardless of its shape.

FIG. 1 presents entire tissue fragments or edges of tissue fragments—patches showing their junction by bringing the shape-matching edges together along the tangential sections.

According to the invention, it is important to adjust the shape of the tissue patch—tissue fragment by planning the course of parallel adjacent edges—the junction site of at least two tissue fragments. This shape exists in all figures, where there are straight edges. This shape can also be partly straight and partly arched at some point. Therefore, the tissue fragments—patches can have any shape. The course of the edge should be compatible—parallel on both connected tissue fragments along the tangential section so that both tissue fragments can be joined along these edges. The edge section or the entire edge of the joined tissue fragments along the tangential section—at the junction of at least two tissue fragments, is referred to as the tangential section.

The principle is that the length on the tangential section of the joined tissue edges—the length of part or the entire edge of the fragment along the tangential section—the junction of tissue fragments should be at least 0.1 cm in length—the length of the tangential section. FIG. 1 shows examples of tangential section shapes: A—rectilinear sections, B—arched sections, as well as examples of shapes of joined tissue fragments: C—angular and geometric tissue fragments, their combinations.

Examples of connections that are not preferred are all types of arc-linear as well as geometric connections with differing angles, where the space between the fragments is relatively large and there are no tangential sections with at least a 0.1 cm long edge of a patch being parallel to the other. They are shown in FIG. 2 FIG. 2 shows examples of non-preferred scrap arrangement—edges are not complementary along the entire length of tangential sections and there are large spaces between the edges. Disadvantages: it is more difficult to fill the space and there is reduced mechanical resistance.

2) Pre-Culture of Tissue Fragments Only.

Selected or appropriately trimmed patches—tissue fragments—slices, as previously described, were transferred into a 1-well, 6-well or 12-well sterile cell culture plate using tweezers. Selected or appropriately trimmed tissue patches were placed in wells previously filled with 10 ml, 2.5 ml or 1.25 ml cell culture medium 1 with 4.5 g/l glucose also known under the trade name DMEM or medium 2 with the addition of 1-fold concentrated solution of Glutamax supplement known under the trade name F12 or a mixture of medium 1 and medium 2 in a ratio of 1:1 and 2%, 4%, 5% or 10% FBS serum and 2 mM-4 mM glutamine.

For this example, culture medium 1, known under the trade name DMEM, was used, containing: calcium anhydrous chloride, iron nitrate hydrate, potassium chloride, magnesium sulphate anhydrous, sodium chloride, sodium bicarbonate, potassium monobasic phosphate monohydrate, D-glucose, L-arginine hydrochloride, L-cystine dihydrochloride, L-glutamine, glycine, L-histidine hydrochloride monohydrate, L-isoleucine, L-leucine, L-lysine hydrochloride, L-methionine, L-phenylalanine, L-serine, L-threonine, L-tryptophan, disodium L-tyrosine dihydrate, L-valine, calcium D-pantothenate, choline chloride, folic acid, i-inositol, niacinamide, riboflavin, thiamine hydrochloride, pyridoxine hydrochloride with 4-(2-hydroxyethyl) piperazine-1 sodium salt-ethanesulfone with glucose added.

For this example, culture medium 2 was used, containing: calcium anhydrous, copper sulphate pentahydrate, ferrous sulphate heptahydrate, magnesium chloride, potassium chloride, sodium bicarbonate, sodium chloride, sodium dibasic anhydrous, zinc sulphate heptahydrate, L-Alanine, L-arginine hydrochloride was used, L-asparagine monohydrate, L-aspartic acid L-cysteine hydrochloride, L-glutamic acid, L-Glutamine, glycine L-Histidine trihydrochloride monohydrate, L-isoleucine, L-Leucine, L-lysine hydrochloride, L-methionine, L-phenylalanine, L-Proline, L-Serine, L-threonine, L-Tryptophan, L-tyrosine dibasic dihydrate, L-valine, D-biotin, choline chloride, folic acid, myo-inositol, niacinamide, D-pantothenic acid (hemicalcium)), pyridoxine hydrochloride, riboflavin, thiamine hydrochloride, vitamin B12, D-glucose, hypoxanthine, linoleic acid, phenolic red, putrescine hydrochloride, monosodium pyruvic acid, thymidine with the addition of 1-fold concentrated Glutamax supplement solution.

For this example, the action of a 1:1 mixture of both media was also checked.

Preferably, the medium contains a minimum of 4.0 g/l glucose, preferably 4.5 g/l glucose, a minimum of 10% FBS and a minimum of 2 mM glutamine.

Preferably, the culture medium should contain 55-75 mg/l sodium pyruvate and sodium bicarbonate, 2 mM-4 mM glutamine, 2%-10% FBS, and at least 4.5 g/l glucose as well as ethanolamine, glutathione, ascorbic acid, insulin, transferrin, copper sulphate, manganese chloride.

A minimum of two tissue flaps patches approximately 1 mm×1 cm×1 cm in size were placed in each well of the culture plate, and arranged so that they adhere to each other along one of their edges along their maximum lengths or fragments of their edges along a tangential section of at least 0.1 cm in length as in the example. Several experiments were carried out using 2-4 fragments with tangential sections of 0.1-0.5-1 cm. Cartilage was incubated for 7 days in 37° C. and 5% CO2. After this time, microscopic observation was carried out and the medium was replaced with fresh one. In the case of a 6-well plate, which was used in this experiment, every time the volume of fresh medium replaced every 7 days was 2.5 ml. An inverted microscope was used to assess the viability of tissue patches; microbiological purity of the culture; the appearance of possible new cellular structures resulting from the division of cells present in the tissue. Junction between two tissue fragments, their viability and proliferation were monitored using 10× and 40× optical magnification.

The tissue fragments were cultured until sufficient number of chondrocytes was obtained (separate culture-adherent culture) to flood the tissue fragments with a suspension of propagated chondrocytes. In this experiment, it was 17 days. The tissue fragment culture involved a kind of incubation and was aimed at maintaining the tissue fragments in active state, ready for the next step taking place already in proper culture with free chondrocytes.

3) Obtaining the Chondrocyte Suspension and Initial Adherent Culture of the Chondrocytes Alone.

Obtaining and culturing chondrocytes to propagate them can be performed using a known method.

After the selection of the tissue patches, which act as the basis for the future new tissue flap, the remaining patches intended for isolation of chondrocytes, constituting from 15% to 50% of the weight of all patches, were used to obtain a chondrocyte suspension. The shape of the tissue fragment does not matter in obtaining chondrocytes. For this purpose, the tissue intended for enzymatic digestion was additionally cut into smaller pieces (not larger than 3 mm×3 mm×3 mm) using a scalpel. The material prepared in this way was treated with collagenase II.

The resulting tissue pieces were transferred to a sterile tube with 15 ml to 50 ml volume. In this case it was a 50 ml tube. Tissue pieces were rinsed 3 times with 1× concentrated phosphate buffered saline (1×PBS). The enzymatic digestion time, as well as the amount of enzyme, was adjusted to the mass of tissue fragments as well as to obtain proper cell viability after the reaction. For this study, the following tissue to enzyme weight ratios ranges were used: 1 g:1 mg, 1 g:2 mg, 1 g:3 mg and 1 g:4 mg. The digestion reaction was carried out in culture medium 1, known under the trade name DMEM, containing: calcium anhydrous chloride, iron nitrate hydrate, potassium chloride, magnesium sulphate anhydrous, sodium chloride, sodium bicarbonate, potassium phosphate monobasic monohydrate, D-glucose, L-arginine hydrochloride, L-cystine dihydrochloride, L-glutamine, glycine, L-histidine hydrochloride monohydrate, L-isoleucine, L-leucine, L-lysine hydrochloride, L-methionine, L-phenylalanine, L-serine, L-threonine, L-tryptophan, disodium L-tyrosine dihydrate, L-valine, calcium D-pantothenate, choline chloride, folic acid, i-inositol, niacinamide, riboflavin, thiamine hydrochloride, pyridoxine hydrochloride) with 4-(2-hydroxyethyl) piperazine sodium salt 1-ethanesulfone with the addition of glucose; or in culture medium 2 containing: calcium anhydrous, copper sulphate pentahydrate, ferrous sulphate heptahydrate, magnesium chloride, potassium chloride, sodium bicarbonate, sodium chloride, anhydrous sodium dibasic phosphate, zinc sulphate heptahydrate, L-Alanine, L-arginine hydrochloride, L-asparagine monohydrate, L-aspartic acid L-cysteine hydrochloride, L-glutamic acid, L-Glutamine, glycine L-Histidine trihydrochloride monohydrate, L-isoleucine, L-Leucine, L-lysine hydrochloride, L-methionine, L-phenylalanine L-Proline, L-Serine, L-threonine, L-Tryptophan, L-tyrosine dibasic dihydrate, L-valine, D-biotin, choline chloride, folic acid, myo-inositol, niacinamide, D-pantothenic acid (hemicalcium), pyridoxine hydrochloride, riboflavin, thiamine hydrochloride, vitamin B12, D-glucose, hypoxanthine, phenolic linoleic acid red, putrescine hydrochloride, monosodium pyruvic acid, thymidine with the addition of a 1-fold concentrated Glutamax supplement solution; or a mixture of the two above-mentioned culture media used in a 1:1 ratio with added glucose.

The tissue was placed in the medium in a ratio of: 3 ml medium:0.1 g tissue or 3 ml medium:0.2 g tissue or 3 ml medium:0.3 g tissue or 3 ml medium:0.5 g of tissue), containing the appropriate concentration of collagenase II. The mass of tissue in grams is the total value consisting of the mass of the used tissue patches. The patches were digested to a maximum of 0.5 g in total.

The patches with the total weight of 0.5 g were digested. Digestion was carried out in 37° C., 5% CO2 in a cell culture incubator. The reaction was carried out for a minimum of 16 hours until the tissue was completely digested. After digestion, the supernatant containing free chondrocytes was removed and centrifuged at 300×g for a minimum of 10 minutes at room temperature. The resulting cell precipitate, containing chondrocytes in the amount of 0.3 million from 1 g of tissue to 1.5 million from 1 g of tissue, was rinsed three times in 1-fold concentrated PBS. The amount of tissue subjected to digestion is usually about 0.1-0.2 g on average. Ultimately, the cell precipitate was resuspended in a minimum of 1 ml medium 1 with 4.5 g/l glucose or medium 2 with the addition of a 1-fold concentrated Glutamax supplement solution or a mixture of medium 1 and medium 2 in a 1:1 ratio, containing 2% or 4% or 5% or 10% FBS and a minimum 2 mM glutamine solution for observation and qualitative and quantitative evaluation of digestion. It was assessed whether after digestion the cells demonstrated good viability (qualitative assessment) and whether the entire tissue fragment was digested (quantitative assessment). Cell viability (minimum viability of 80% was treated as positive), shape and overall condition of cells after digestion (round with visible nucleus were treated as cells in good condition) were subject to qualitative assessment. Cells with a viability of not less than 80% were seeded into 25 cm2 or 75 cm2 culture bottles at densities of 150,000 cells per 2 ml medium or 200,000 cells per 2 ml medium or 250,000 cells per 2 ml medium. During culture, every other day, cells were observed using an inverted optical microscope to assess the growth rate and determine the moment of cell passage, closely related to the level of confluence. The culture medium was replaced twice a week. When the cells reached the appropriate confluence (maximum 85%), they were trypsinized for 5 minutes with a 2 ml 0.05% (w/v) solution of trypsin/EDTA in PBS in 37° C. Trypsinization inhibition was carried out by the addition of medium 1 with the addition of glucose 4.5 g/l or medium 2 with the addition of a 1-fold concentrated Glutamax supplement solution or a mixture of medium 1 and medium 2 in a 1:1 ratio containing 2%, 4%, 5% or 10% FBS in a volume of 1, 1.5 or 2 times the volume of the used trypsin/EDTA solution. Cell numbers and viability were determined using a microscope and trypan blue solution according to a standard procedure.

Cell growth and viability were primarily monitored during chondrocyte culture. The culture was continued until 85% confluency at min. 80% cell viability. The purpose of this culture was to multiply a sufficient number of cells for the next combined culture of tissue fragments with chondrocytes, i.e. "tissue flooding", where the chondrocyte suspension serves as an adhesive for joining the tissue fragments. Some of the cells were used to "flood" the tissue and some were used to establish another culture so that the cell material was still available.

The cells remained in continuous culture for use in stimulating connections between the pieces of cartilage tissue described in point a).

Culturing chondrocytes for the purpose of their multiplication is always carried out in monolayer—adherent culture. We talk about cell suspension when, after the cells have been detached from the surface of the plate, the washing and centrifugation steps are carried out, as well as the suspension of chondrocytes in the target buffer and flooding the flaps tissue patches in the combined culture.

4) Combined Culture—Tissue Fragments with Chondrocyte Suspension According to Point 3.

It is important to add a minimum of 40,000 chondrocytes to a well containing 2.5 ml of culture medium with the assumption that two tissue patches with the size of about 1 mm×1 cm×1 cm are used. The maximum chondrocyte concentration for culturing two fragments with a tangential segment length of 0.1 cm is 8000 chondrocytes per 2.5 ml medium.

Cartilage tissue patches, cultured in medium 1 with 4.5 g/l glucose or medium 2 with the addition of 1-fold concentrated Glutamax supplement solution or medium 1 and medium 2, described above, in a 1:1 ratio with 2% or 4% or 5% or 10% FBS, with a minimum of 2 mM glutamine and a minimum of 0.01% IGF-1 and/or a minimum of 0.01% TGF-β1 and/or a minimum of 0.01% chondroitin and/or a minimum of 0.1% insulin was "flooded" with chondrocytes obtained from culture after digestion (viability ≥85% minimum).

It is important that the medium contains a minimum of 4.5 g/l glucose, a minimum of 10% FBS and a minimum of 2 mM glutamine.

Preferably, the culture medium should contain 55-75 mg/l sodium pyruvate and sodium bicarbonate, 2 mM-4 mM glutamine, 2%-10% FBS, and at least 4.5 g/l glucose as well as ethanolamine, glutathione, ascorbic acid, insulin, transferrin, copper sulphate, manganese chloride and a minimum of 0.01% IGF-1 and/or a minimum of 0.01% TGF 31 and/or a minimum of 0.01% chondroitin and/or a minimum of 0.1% insulin.

After centrifugation and prior quantitative and qualitative assessment as described above, the cells were suspended in medium 1 with 4.5 g/l glucose or medium 2 with the addition of a 1-fold concentrated Glutamax supplement solution or medium 1 and medium 2 in a ratio of 1:1 in a volume of a minimum of 500 μl for a minimum of 40,000 cells, after which they were added to a well with a minimum of two tissue fragments. It is important that the culture medium contains 55 mg/l-75 mg/l sodium pyruvate, sodium bicarbonate, 2 mM-4 mM glutamine, 2%-10% FBS, and 4.5 g/l-5.0 g/l glucose.

The resulting combined culture of tissue fragments and chondrocytes was cultured in 37° C., 5% CO2 in a cell culture incubator for a minimum of 12 weeks until new tissue connections were obtained between the tissue fragments. The process of "flooding" the tissue with the suspension containing a constant amount of chondrocytes every time was repeated once a week. The replacement of the medium with the indicated frequency was dictated by the experience gained in tissue cultures. The addition of chondrocytes took place after gentle transfer of tissue fragments to a new well of a 6-well plate. The medium was also replaced at that time, in the case of a 6-well plate it was the final volume of 2.5 ml including supplements.

Tissue modifications: connection, viability and proliferation were observed regularly, before each subsequent tissue 'flooding' with cells, using an inverted optical microscope at 10× and 40× magnification. Culture medium and supplements were changed once a week.

With each subsequent "flooding" with new chondrocytes, the following actions were performed:

1) removing the old medium
2) gentle transfer of tissue slices to a new culture plate
3) addition of fresh medium
4) Flooding the patches with cells (with the aforementioned number of cells and medium, in which they are suspended—per the now provided volume of fresh medium)—description above.

After several days of test culture, visible changes were noticed in cartilage tissue. New tissue connections between old tissue fragments were identified. After a few weeks, the gap between the old pieces of tissue was filled with new tissue and overgrown. A flap patch of new tissue was obtained, formed from cartilage patches and free chondrocytes regularly supplied to the culture. One new tissue flap patch obtained from initial two tissue patches had a "furrow" in the middle, presumably of new tissue, formed with the participation of chondrocytes regularly supplied to the culture in the form of a suspension. The tissue flap was about 1 mm×2.1 cm×1 cm. It was possible to transfer it from the plate well to another destination without the need to use two pairs of tweezers and without the risk of damage. The new connection between the initial tissue patches had a slightly lighter colour compared to the old tissue, as shown in FIG. 3—inverted microscopy image on the day of starting the culture (FIG. 3 A), after seventeen days (FIG. 3 B) and fifty-two days (FIG. 3 C, D) of the cell-tissue culture using two tissue fragments with tangential section.

Throughout the period of proper culture, which was a combined culture of tissue patch and cell suspension, as described above, a separate chondrocyte suspension culture was performed simultaneously. The cell suspension culture was necessary for the constant maintenance of the source of cellular material used to "flood" tissue patches. Observations were made at a 40× magnification.

FIG. 3 shows a microscopic image of tissue patch culture in medium 1 with 4.5 g/l glucose, 10% FBS, 2 mM glutamine, as described above—visualization of new tissue formation over time. A: Image of fragments of two tissue patches as closely adjacent to each other as possible along the tangential section of about 1 cm in length on the first day of culture (image documenting the culture baseline, day 1). Clearly visible free space between the contact surfaces of two tissue patches. B: Image of fragments of two tissue patches, adhering to each other along the tangential section of about 1 cm and visible tissue filling, being formed between the contact surfaces of two tissue patches on the seventeenth day of culture in medium 1 with the addition of 4.5 g/l glucose, 10% FBS and 2 mM glutamine. C, D: Image of fragments of two tissue patches, adhering to each other along the tangential section of about 1 cm and visible tissue filling, formed between the contact surfaces of two tissue patches on the fifty second day of culture in medium 1 with the addition of 4.5 g/l glucose, 10% FBS and 2 mM glutamine. The new tissue formed after fifty two days of culture clearly scars the free space at the junction of two tissue patches present on the first day of culture. Significant alignment of the old and new tissue colour at one end of the two contact surfaces of the tissue patch fragments is visible. Image taken using 10× magnification (A, B, C) and 40× magnification (D).

Example 5—a Variant of Invention Application

Culture is carried out as described in Example 4, with the following conditions changed to a certain extent:

1) Obtaining of Cartilage Tissue Fragments for Further Culture.

Eight patches of oval-shaped tissue were obtained, but each lobe was cut on one side to allow the largest contact area between two adjacent fragments. The obtained patches were thin, only about 1 mm thick. They were about 0.9 cm long and about 0.5-0.6 cm wide.

2) Pre-Culture of Tissue Fragments Only

Selected and appropriately trimmed patches, as described above, were transferred into a well or 6-well sterile cell culture plate using tweezers. Two selected tissue patches, approximately 1 mm thick, 0.9 cm long and 0.6 cm wide, were placed in a well previously filled with 2.5 ml of medium 1 and medium 2 with 4.5 g/l glucose, 10% FBS serum, 55 mg/l sodium pyruvate and 2 mM glutamine. The tangential section was rectilinear. Medium 1 and 2 have been described in the previous example.

Two patches of tissue per well were placed in three wells of the culture plate, arranged in such a way that one edge of each patch (tangential edge) with the length of about 0.6 cm adhered to another as closely as possible. These were biological replicates of the same test. Cartilage was incubated for 7 days in 37° C. and 5% CO2. The culture medium was replaced every 7 days, using an inverted microscope every time to assess the viability of tissue patches; microbiological purity of the culture and analyse the appearance of possible new cellular structures resulting from the division of cells present in the tissue. 10× and 40× optical magnification was used. Observations were made before the medium replacement.

3) Obtaining of Chondrocyte Suspension and Culture

The other two patches (size: approx. 1 mm×0.9 cm×0.5 cm) were intended for isolation of chondrocytes, in total they constituted approx. 25% of the weight of all patches. For this purpose, the tissue intended for enzymatic digestion was additionally cut into smaller pieces (about 2 mm×2 mm×2 mm in size) using a scalpel. The material prepared in this way was treated with collagenase II. The resulting tissue pieces were transferred to a 30 ml sterile tube. Tissue pieces were rinsed 3 times with 1× concentrated phosphate buffered saline (1×PBS). For this study, the following tissue to enzyme weight ratio was used: 1 g:1 mg. The digestion reaction was carried out under the following conditions: mixture of medium 1 and medium 2 with the addition of 4.5 g/l glucose (in a ratio of 3 ml medium per 0.3 g tissue—i.e. 2 ml), containing the appropriate amount of collagenase II, i.e. 0.2 mg. The mass of tissue in grams was the total value of the mass of the used tissue patches. Digestion was carried out in 37° C., 5% CO2 in a cell culture incubator. The reaction was carried out for 20 hours overnight. After digestion, the supernatant containing free chondrocytes was collected and centrifuged at 300×g for 10 minutes at room temperature (21° C.). The resulting cell precipitate containing chondrocytes was rinsed three times in 1-fold concentrated PBS. Finally, the cell precipitate was resuspended in a 1 ml mixture of medium 1 and medium 2 with the addition of 4.5 g/l glucose, 10% FBS and 2 mM glutamine for observation and qualitative assessment (mainly the assessment of cell viability and cell condition after digestion—e.g. Shape regularity was assessed) as well as quantitative digestion reaction. A chondrocyte suspension with 98% viability containing 0.49 million viable cells was obtained. The obtained cells were then seeded at a density of 10,000 cells per cm2. The cells were seeded in 6-well plates and a 25 cm2 culture bottle.

The cells remained in continuous culture for use in stimulating connections between the pieces of cartilage tissue.

4) Combined Culture—Tissue Fragments with Chondrocyte Suspension

The cartilage tissue patches described in point 2 of this example, grown in a mixture of medium 1 and medium 2 with the addition of 4.5 g/l glucose, 10% FBS, 2 mM glutamine, 55 mg/l pyruvate were "flooded" with chondrocytes obtained as a result of culture after digestion (viability in the range of 85%-92%). After centrifugation and prior quantitative and qualitative assessment as described above (point 3 of this example), the cells were suspended in a mixture of medium 1 and medium 2 with the addition of 4.5 g/l glucose in the final volume of 1000 μl and the suspension containing 80 000 cells was added to each well with two tissue patches. Next, the supplements were added. In this study, they were IGF-1 and TGF at the final concentration in the well amounting to 0.01% for both supplements.

The resulting combined culture of tissue fragment and chondrocytes was cultured in 37° C., 5% CO2 in a cell culture incubator for 5 weeks until new tissue connections were obtained between the tissue fragments. The process of "flooding" the tissue with the suspension containing a constant amount of chondrocytes (80,000 cells per 2.5 ml medium per well containing two tissue patches) was repeated weekly (every 7 days). Before tissue transfer and the addition of fresh medium and chondrocytes, the tissue patches were subjected to observation (as described in Example 4). The addition of chondrocytes took place after gentle transfer of tissue fragments to a new well of a 6-well plate.

After seven days of test culture, visible changes were noticed in cartilage tissue. After nineteen days, tissue connections between old tissue fragments were identified, as presented in FIG. 4—inverted microscopy image taken on the day of starting the culture (FIG. 4 A) and after nineteen days of cell-tissue culture (FIG. 4 B) using two tissue fragments with 0.6 cm tangential section. The new connections between the patches looked like fibres binding the patches. After five weeks, the gap between the old pieces of tissue was filled with new tissue and overgrown. The junction of two tissue patches was filled with new cellular connections. The new tissue between the cartilage patches took the form of a kind of "scar". On microscopic images, the new tissue is brighter than the tissue of the original cartilage patches. A flap patch of new tissue was obtained, formed from cartilage patches and free chondrocytes regularly supplied to the culture. A new tissue flap of about 1 mm×1.8 cm×0.6 cm was obtained.

FIG. 4. presents a microscopic image of tissue patch culture in a mixture of medium 1 and 2—visualization of the formation of new tissue connections over time. A: Image of fragments of two tissue patches as closely adjacent to each other as possible along a section of 0.6 cm in length on the first day of culture (image documenting the culture baseline). Clearly visible free space between the contact surfaces of two tissue patches. B: Image of fragments of two tissue patches, adhering to each other along a section of about 0.6 cm and visible tissue connection, being formed between the contact surfaces of two tissue patches on the nineteenth day of culture in a mixture of medium 1 and medium 2 with the addition of 4.5 g/l glucose, 10% FBS, 2 mM glutamine and supplements: IGF-I and TGF at a concentration of 0.01%. New tissue is visible, both on the surface of one of the adjacent fragments and between the fragments of the tissue patches. The resulting connections have the nature of fibres connecting two contact surfaces with each other. Image taken using 10× magnification.

Example 6—a Variant of Invention Application

Culture is carried out as described in examples 4 and 5 except that:

1) Obtaining of Cartilage Tissue Fragments for Further Culture:

Ten oval-shaped tissue patches were obtained, but each flap was cut on two sides (the longest ones). The obtained patches were about 3 mm thick. They were about 1 cm long and about 0.2 cm wide.

2) Pre-Culture of Tissue Fragments Only:

Selected and appropriately trimmed patches, as described above, were transferred into a well or 6-well sterile cell culture plate using tweezers. Four selected tissue patches, about 3 mm thick, about 1 cm long (the length of the tangential surface—in each of the fragments, the shape of the surface provided maximum compatible contact surface, almost rectilinear) and about 0.2 cm wide were placed in a well previously filled with 1.25 ml of the culture medium 1 and 2 mixture with the addition of 4.5 g/l glucose, 2% FBS serum and 2 mM glutamine.

The tangential section between each pair was about 1 cm.

Four patches of tissue per well were placed in three wells of a 12-well culture plate, arranged in such a way that one edge of each patch (tangential edge) with the length of about 1 cm adhered to another as closely as possible.

3) Obtaining of Chondrocyte Suspension and Culture:

For this study, the following tissue to enzyme weight ratio was used: 1 g:2 mg. The digestion reaction was carried out under the following conditions: mixture of medium 1 and medium 2 with the addition of 4.5 g/l glucose (in a ratio of 3 ml medium per 0.3 g tissue—i.e. 2 ml), containing the appropriate amount of collagenase II, i.e. 0.4 mg. The reaction was carried out for 14 hours. Finally, the cell precipitate was resuspended in a 1 ml mixture of medium 1 and medium 2 with the addition of 4.5 g/l glucose, 2% FBS and 2 mM glutamine for observation and qualitative assessment (mainly the assessment of cell viability and cell condition after digestion—e.g. Shape regularity was assessed) as well as quantitative digestion reaction. A chondrocyte suspension with 92% viability containing 0.42 million viable cells was obtained.

4) Combined Culture—Tissue Fragments with Chondrocyte Suspension

The cartilage tissue patches described in point 2 of this example, grown in a mixture of medium 1 and medium 2 with the addition of 4.5 g/l glucose, 2% FBS and 2 mM glutamine were "flooded" with chondrocytes obtained as a result of culture after digestion (viability in the range of 85%-92%). An appropriate volume of suspension containing 80,000 cells/1.25 ml medium was added to the well with the tissue patches. Next, the supplements were added. In this study it was chondroitin at the final concentration in the medium in the well amounting to 0.01%.

The resulting combined culture of tissue fragments and chondrocytes was incubated at 37° C., 5% CO2 in a cell culture incubator for a total of 8 weeks until new tissue connections were obtained between the tissue fragments used. The process of "flooding" the tissue with the suspension containing a constant amount of chondrocytes (80,000 cells per well containing two tissue patches) was repeated weekly (every 7 days). Before tissue transfer and the addition of fresh medium and chondrocytes, the tissue patches were subjected to observation (as described in Example 4). The addition of chondrocytes took place after gentle transfer of tissue fragments to a new well of a 12-well plate.

After fourteen days of test culture, visible changes were noticed in cartilage tissue. After nineteen days, tissue connections between old tissue fragments were identified, as presented in FIG. 5—inverted microscopy image taken on the day of starting the culture (FIG. 5 A) and after seven days of cell-tissue culture (FIG. 5 B, C) using four tissue fragments with 1 cm tangential section.

The new connections between the patches looked like fibres binding the patches. After seven weeks, the gap between the old pieces of tissue were filled with new tissue and overgrown. The junctions of two tissue patches were filled with new cellular connections. A flap patch of new tissue was obtained, formed from cartilage patches and free chondrocytes regularly supplied to the culture. A new tissue flap of about 3 mm×1 cm×0.8 cm was obtained.

FIG. 5 presents a microscopic image of tissue patch culture (first and second) in medium 1—visualization of the formation of new tissue connections over time. A: Image of fragments of two tissue patches (first and second) as closely adjacent to each other as possible along a section of 1 cm in length on the first day of culture (image documenting the culture baseline). There is free space between the first tissue patch located closest to the edge of the plate and the next adjacent tissue patch. The first fragment was gently cut at the edge of the tangential surface to be identified in the subsequent stages of experiment (the first patch fragment is at the bottom of the image). B, C: Image of fragments of two tissue patches (first and second) and visible tissue connections formed between the contact surfaces, about 1 cm long, of two tissue patches on the twenty-seventh day of culture in medium 1 with the addition of 4.5 g/l glucose, 2% FBS, 2 mM glutamine and chondroitin at a concentration of 0.01%. Fibre-like connections form between the contact surfaces of the tissue patches. In the following days of culture, new tissue will form between them permanently binding two tissue patches. Connections of the same type were also observed between the second and third, and the third and fourth patches, respectively. Images [A, B] taken at 10× magnification, image [C] with 40× magnification.

Example 7—a Variant of Invention Application

Culture is carried out as described in Example 5 except that:

1) Obtaining of Cartilage Tissue Fragments for Further Culture:

Five rectangular tissue patches were obtained. The obtained patches were about 2 mm thick. They were about 0.5 cm long and about 0.4 cm wide.

2) Pre-Culture of Tissue Fragments Only:

Selected and appropriately trimmed patches, as described above, were transferred into a well or 6-well sterile cell culture plate using tweezers. Three selected tissue patches, approximately 2 mm thick, 0.5 cm long and 0.4 cm wide (contact surface length), were placed in a well previously filled with 2.5 ml of culture medium 2 with 4% FBS serum pyruvate and 2 mM glutamine. The above tissue patches were oval in shape, with two of the three patches having a convex contact surface and one patch with two concave surfaces. All contact surfaces were compatible with each other, i.e. they were as close to each other as possible.

Three patches of tissue per well were placed in three wells of a 6-well culture plate, arranged in such a way that one edge of each patch (tangential edge) with the length of about 0.4 cm adhered to another as closely as possible.

3) Obtaining of Chondrocyte Suspension and Culture:

For this study, the following tissue to enzyme weight ratio was used: 1 g:4 mg. The digestion reaction was carried out under the following conditions: mixture of medium 1 and medium 2 with the addition of 4.5 g/l glucose (in a ratio of 6 ml medium per 0.3 g tissue—i.e. 4 ml), containing the appropriate amount of collagenase II, i.e. 0.8 mg. The reaction was carried out for 8 hours. Finally, the cell precipitate was resuspended in a 1 ml of medium 2 with the addition of 4.5 g/l glucose, 4% FBS and 2 mM glutamine for observation and qualitative assessment (mainly the assessment of cell viability and cell condition after digestion—e.g. Shape regularity was assessed) as well as quantitative digestion reaction. A chondrocyte suspension with 86% viability containing 0.32 million viable cells was obtained.

4) Combined Culture—Tissue Fragments with Chondrocyte Suspension

The cartilage tissue patches described in point 2 of this example, grown in a medium 2 with the addition of 4.5 g/l glucose, 4% FBS and 2 mM glutamine were "flooded" with chondrocytes obtained as a result of culture after digestion (viability in the range of 85%-92%). An appropriate volume of suspension containing 60,000 cells was added to the well with the tissue patches. Next, the supplements were added. In this study it was insulin at the final concentration in the medium in the well amounting to 0.2%.

The resulting combined culture of tissue fragment and chondrocytes was cultured in 37° C., 5% CO2 in a cell culture incubator for 11 weeks until new tissue connections were obtained between the tissue fragments. The process of "flooding" the tissue with the suspension containing a constant amount of chondrocytes (60,000 cells per well containing three tissue patches) was repeated weekly (every 7 days). Before tissue transfer and the addition of fresh medium and chondrocytes, the tissue patches were subjected to observation (as described in Example 4). The addition of chondrocytes took place after gentle transfer of tissue fragments to a new well of a 6-well plate.

After twenty one days of test culture, visible changes were noticed in cartilage tissue. After forty-three days, new tissue connections between old tissue fragments were identified in all tissue patches, i.e. between the first and second as well as the second and third. After eleven weeks, the gap between the old pieces of tissue were filled with new tissue and overgrown. The junction of three tissue patches was filled with new cellular connections. A flap patch of new tissue was obtained, formed from cartilage patches and free chondrocytes regularly supplied to the culture. A new tissue flap of about 2 mm×1.5 cm×0.4 cm was obtained.

This invention further pertains to following items:

1. A method of in vitro chondrocyte cell culture to obtain material for the treatment of articular cartilage defects, characterized by cutting the obtained hyaline cartilage obtained into at least two tissue fragments, which are then arranged on a culture plate next to each other in a culture medium containing a minimum of 2 mM glutamine, a minimum of 2% FBS and a minimum of 4.5 g/l glucose, with the shape of the tissue fragments being adjusted at least along one edge section of each fragment so that after placing the fragments close together the space between the two similar tissue fragments is as small as possible and so that the space of the culture plate containing tissue fragments is as small as possible in order to join fragments along at least one tangential section during culture through the addition of chondrocyte suspension to the culture and continuing the cell culture of tissue fragments with chondrocytes, replacing the culture medium at fixed times and adding chondrocytes to the culture medium. The cultures are continued until the tissue fragments form a juncture at least along the tangential section.
2. The method according to item 1 characterised in the culture medium containing supplements at a concentration of minimum 0.01% IGF and/or 0.01% TGF and/or 0.01% chondroitin and/or a minimum of 0.1% insulin.
3. The method according to item 1 or 2 characterized in the culture medium containing 55-75 mg/l sodium pyruvate and sodium bicarbonate, 2 mM-4 mM glutamine, 2%-10% FBS, and at least 4.5 g/l glucose as well as ethanolamine and/or glutathione and/or ascorbic acid and/or insulin and/or transferrin and/or copper sulphate and/or manganese chloride.
4. The method according to item 1 or 2 or 3 characterized in culturing only the tissue fragments in the medium, preferably for at least 14 days before the adding chondrocytes to the culture.
5. The method according to item 1 or 4 characterized in adding chondrocyte suspensions to the tissue fragments in such an amount that at least 40,000 chondrocytes are present per 2.5 ml of culture medium.
6. The method according to item 1 or 4 or 5 characterized in the minimum chondrocyte concentration for culturing two fragments with a tangential segment length of 0.1 cm-1 cm being 40,000 chondrocytes per 2.5 ml medium.
7. The method according to item 1 characterized in obtaining the cultured chondrocytes by enzymatic digestion, after which the required number of cells is obtained by culturing chondrocytes in monolayer in adherent culture.
8. The method according to item 1 characterized in culturing the cells in the temperature increased to 37° C. and 5% CO2.
9. The method according to any one of items 1-8, characterized in the tangential section between at least two joined tissue fragments being minimum 0.1 cm, most preferably at least 0.5 cm.
10. The method according to any one of items 1-19, characterized in the tissue fragments having an oval-like shape.
11. The method according to any one of items 1-10, characterized in the shape of the tissue fragments being selected so that the tissue fragments in culture adhere very closely to each other along the tangential section.

The invention claimed is:

1. A method for producing a cartilage tissue implant in vitro, the method comprising:

i) providing at least a first and a second fragment of viable cartilage tissue, which each have at least one edge, wherein one edge of the first fragment is complementary in shape to one edge of the second fragment, wherein the first fragment and the second fragment of viable cartilage tissue comprise viable chondrocytes;

ii) placing the fragments in a culture medium such that at least one edge of the first fragment is spaced 1 cm or less apart from at least one edge of the second fragment;

iii) adding a suspension of viable chondrocytes to the fragments from step (ii); and iv) cultivating the fragments and chondrocytes under cell culture conditions to thereby produce a cartilage tissue implant in vitro, wherein the edges of the fragments are in contact with each other along a tangential section, and wherein the tangential section of contact has a length of at least 0.5 cm.

2. The method according to claim 1, wherein the culture medium comprises a buffer, one or more salts, amino acids, and one or more of: galactose, dextransulfate, spermidine, beta-glycerolphosphate and adenine.

3. The method according to claim 1, wherein the medium further comprises growth factors from human and/or calf serum.

4. The method according to claim 1, wherein the culture medium comprises Insulin Growth Factor (IGF) and/or Transforming Growth Factor (TGF).

5. The method according to claim 1, wherein the fragments are cultured in the culture medium for at least 14 days after step (ii) before adding the suspension of chondrocytes in step (iii).

6. The method according to claim 1, wherein the viable chondrocytes are added to the culture medium in step (iii) to a final concentration of at least 4,000 chondrocytes per ml of culture medium.

7. The method according to claim 1, wherein the suspension of viable chondrocytes is obtained by enzymatic digestion, wherein the enzymatic digestion is with a protease.

8. The method of claim 1, wherein the viable chondrocytes are cultured in an adherent monolayer prior to being suspended.

9. The method according to claim 1, wherein cultivation temperature is between 35-38° C., and/or $CO_2$ concentration is between 4-6%.

10. The method according to claim 4, wherein the culture medium comprises a minimum of 0.01% IGF and/or 0.01% TGF.

11. The method according to claim 6, wherein the viable chondrocytes are added to the culture medium in step (iii) to a final concentration of 4,000 to 40,000 chondrocytes per ml of culture medium.

12. The method according to claim 11, wherein the viable chondrocytes are added to the culture medium in step (iii) to a final concentration of 20,000 to 40,000 chondrocytes per ml of culture medium.

13. The method according to claim 1, wherein step (iv) comprises periodically flooding the fragments with additional suspensions of viable chondrocytes.

14. The method according to claim 13, wherein step (iv) comprises flooding the fragments with additional suspensions of viable chondrocytes once every seven days.

15. The method according to claim 1, wherein the first fragment and the second fragment of cartilage tissue are hyaline cartilage tissue.

16. The method according to claim 1, wherein the first and second fragments of viable cartilage tissue were obtained from an autologous source.

17. A method of repairing damaged hyaline cartilage tissue in a patient in need thereof comprising:

i) obtaining at least a first and a second fragment of viable hyaline cartilage tissue from the patient, which each have at least one edge, wherein one edge of the first fragment is complementary in shape to one edge of the second fragment, wherein the first fragment and the second fragment of viable hyaline cartilage tissue comprise viable chondrocytes;

ii) placing the fragments in a culture medium such that the edges of the fragments are in contact with each other along a tangential section, and wherein the tangential section of contact has a length of at least 0.1 cm;

iii) adding a suspension of viable chondrocytes to the fragments from step (ii);

iv) cultivating the fragments and chondrocytes under cell culture conditions to thereby produce a cartilage tissue implant in vitro; and v) repairing damaged hyaline cartilage tissue in the patient by implanting the cartilage tissue implant in the patient.

18. The method of claim 17, wherein the damaged hyaline cartilage tissue is in a patient with a disease selected from osteoarthritis, rheumatoid arthritis, spondyloarthritis, juvenile idiopathic arthritis, lupus, gout, and bursitis.

* * * * *